United States Patent
Parmer et al.

(10) Patent No.: US 9,271,785 B2
(45) Date of Patent: Mar. 1, 2016

(54) VAGINAL REMODELING DEVICE AND METHODS

(75) Inventors: Jonathan B. Parmer, Woodside, CA (US); Ian F. Smith, Sunnyvale, CA (US); Chun-Chih Cheng, Sunnyvale, CA (US); Patrick Karl Howe, Hollister, CA (US); Sean Yasuo Sullivan, Santa Clara, CA (US); Jerome Jackson, Los Altos, CA (US); Stanley Levy, Jr., Saratoga, CA (US); Sherree Leigh Lucas, Berkeley, CA (US); Steven Marc Lopez, Los Altos, CA (US)

(73) Assignee: Viveve, Inc., Sunnyvale, CA (US)

( * ) Notice: Subject to any disclaimer, the term of this patent is extended or adjusted under 35 U.S.C. 154(b) by 877 days.

(21) Appl. No.: 12/884,108

(22) Filed: Sep. 16, 2010
(Under 37 CFR 1.47)

(65) Prior Publication Data

US 2011/0178584 A1    Jul. 21, 2011

Related U.S. Application Data

(60) Provisional application No. 61/243,686, filed on Sep. 18, 2009.

(51) Int. Cl.
*A61B 18/04* (2006.01)
*A61B 18/14* (2006.01)
(Continued)

(52) U.S. Cl.
CPC ... *A61B 18/1485* (2013.01); *A61B 2017/00084* (2013.01); *A61B 2018/00023* (2013.01);
(Continued)

(58) Field of Classification Search
CPC ............ A61B 2018/00666; A61B 2018/00797; A61B 2018/00803; A61B 2018/00815; A61B 2018/00821; A61B 2018/00452; A61B 2018/0047; A61B 2018/00476; A61B 2018/00458; A61B 2018/00559

USPC ......................................... 606/24, 32, 34, 41
See application file for complete search history.

(56) References Cited

U.S. PATENT DOCUMENTS

| 4,326,529 A | 4/1982 | Doss et al. |
| 4,381,007 A | 4/1983 | Doss |

(Continued)

FOREIGN PATENT DOCUMENTS

| JP | H05-269144 | 10/1993 |
| JP | H09-122141 | 5/1997 |

(Continued)

OTHER PUBLICATIONS

VOS et al.; Non-ablative hyperthermic mesenchymal regeneration: a proposed mechanism of action based on Vivev model; Energy-Based Treatment of Tissue and Assessment VI, Proc. of SPIE; Bellingham, WA; vol. 7901; No. 1; pp. 1-8; Feb. 10, 2011.

(Continued)

*Primary Examiner* — Ronald Hupczey, Jr.
(74) *Attorney, Agent, or Firm* — Shay Glenn LLP

(57) ABSTRACT

This invention relates generally to apparatus and methods for tightening tissue of the female genitalia by heating targeted connective tissue with radiant energy, while cooling the mucosal epithelial surface over the target tissue to protect it from the heat. Embodiments include a handle and treatment tip that has both an energy delivery element and a cooling mechanism. The handle may be a two-handed handle allowing control even while rotating and maneuvering the treatment around the genital opening. The apparatus or system may also include an integrated controller, which may confirm tissue contact without applying RF energy, based only on the temperature of the applicator and the time since the last application of energy from the applicator.

18 Claims, 28 Drawing Sheets

(51) Int. Cl.
*A61B 17/00* (2006.01)
*A61B 18/00* (2006.01)
*A61B 19/00* (2006.01)
*A61H 19/00* (2006.01)
*A61H 21/00* (2006.01)
*A61H 23/02* (2006.01)

(52) U.S. Cl.
CPC . *A61B2018/00559* (2013.01); *A61B 2019/465* (2013.01); *A61H 19/00* (2013.01); *A61H 21/00* (2013.01); *A61H 23/0245* (2013.01); *A61H 2201/0153* (2013.01); *A61H 2201/0207* (2013.01); *A61H 2201/0214* (2013.01); *A61H 2201/0221* (2013.01); *A61H 2201/0242* (2013.01); *A61H 2201/0292* (2013.01); *A61H 2201/10* (2013.01); *A61H 2201/5038* (2013.01); *A61H 2201/5097* (2013.01); *A61H 2230/50* (2013.01)

(56) References Cited

U.S. PATENT DOCUMENTS

| | | | |
|---|---|---|---|
| 4,785,807 A | 11/1988 | Blanch | |
| 4,785,828 A | 11/1988 | Maurer | |
| 4,907,589 A | 3/1990 | Cosman | |
| 4,920,978 A | 5/1990 | Colvin | |
| 4,976,709 A | 12/1990 | Sand | |
| 5,046,511 A | 9/1991 | Maurer et al. | |
| 5,143,063 A | 9/1992 | Fellner | |
| 5,160,334 A * | 11/1992 | Billings et al. | 606/34 |
| 5,230,349 A | 7/1993 | Langberg | |
| 5,242,440 A | 9/1993 | Shippert | |
| 5,301,692 A | 4/1994 | Knowlton | |
| 5,330,469 A * | 7/1994 | Fleenor | 606/40 |
| 5,334,193 A | 8/1994 | Nardella | |
| 5,348,554 A | 9/1994 | Imran et al. | |
| 5,450,293 A | 9/1995 | Hoffman | |
| 5,458,596 A | 10/1995 | Lax et al. | |
| 5,469,857 A * | 11/1995 | Laurent et al. | 600/523 |
| 5,569,242 A | 10/1996 | Lax et al. | |
| 5,660,836 A | 8/1997 | Knowlton | |
| 5,673,695 A * | 10/1997 | McGee et al. | 600/374 |
| 5,755,753 A | 5/1998 | Knowlton | |
| 5,765,567 A | 6/1998 | Knowlton | |
| 5,824,076 A | 10/1998 | Knowlton | |
| 5,836,990 A * | 11/1998 | Li | 607/28 |
| 5,871,524 A | 2/1999 | Knowlton | |
| 5,919,219 A | 7/1999 | Knowlton | |
| 5,937,863 A | 8/1999 | Knowlton | |
| 5,947,891 A | 9/1999 | Morrison | |
| 5,948,011 A | 9/1999 | Knowlton | |
| 5,951,550 A | 9/1999 | Shirley et al. | |
| 5,954,717 A | 9/1999 | Behl et al. | |
| 6,002,968 A | 12/1999 | Edwards | |
| 6,024,743 A | 2/2000 | Edwards | |
| 6,035,238 A | 3/2000 | Ingle et al. | |
| 6,044,847 A | 4/2000 | Carter et al. | |
| 6,081,749 A | 6/2000 | Ingle et al. | |
| 6,091,995 A | 7/2000 | Ingle et al. | |
| 6,139,569 A | 10/2000 | Ingle et al. | |
| 6,156,060 A | 12/2000 | Roy et al. | |
| 6,216,704 B1 | 4/2001 | Ingle et al. | |
| 6,236,891 B1 | 5/2001 | Ingle et al. | |
| 6,241,753 B1 | 6/2001 | Knowlton | |
| 6,277,116 B1 | 8/2001 | Utely et al. | |
| 6,283,987 B1 | 9/2001 | Laird et al. | |
| 6,292,700 B1 | 9/2001 | Morrison et al. | |
| 6,311,090 B1 | 10/2001 | Knowlton | |
| 6,322,584 B2 | 11/2001 | Ingle et al. | |
| 6,350,276 B1 | 2/2002 | Knowlton | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,413,255 B1 | 7/2002 | Stern | |
| 6,416,504 B2 | 7/2002 | Mosel et al. | |
| 6,425,912 B1 | 7/2002 | Knowlton | |
| 6,427,089 B1 | 7/2002 | Knowlton | |
| 6,430,446 B1 | 8/2002 | Knowlton | |
| 6,438,424 B1 | 8/2002 | Knowlton | |
| 6,453,202 B1 | 9/2002 | Knowlton | |
| 6,461,332 B1 | 10/2002 | Mosel et al. | |
| 6,461,378 B1 | 10/2002 | Knowlton | |
| 6,470,216 B1 | 10/2002 | Knowlton | |
| 6,478,791 B1 | 11/2002 | Carter et al. | |
| 6,480,746 B1 | 11/2002 | Ingle et al. | |
| 6,482,204 B1 | 11/2002 | Lax et al. | |
| 6,533,780 B1 | 3/2003 | Laird et al. | |
| 6,546,934 B1 | 4/2003 | Ingle et al. | |
| 6,558,381 B2 | 5/2003 | Ingle | |
| 6,569,160 B1 * | 5/2003 | Goldin et al. | 606/41 |
| 6,572,639 B1 | 6/2003 | Ingle et al. | |
| 6,579,266 B2 | 6/2003 | Mosel et al. | |
| 6,587,731 B1 | 7/2003 | Ingle et al. | |
| 6,629,535 B2 | 10/2003 | Ingle et al. | |
| 6,685,623 B2 | 2/2004 | Presthus et al. | |
| 6,743,165 B2 | 6/2004 | Mosel et al. | |
| 6,749,624 B2 | 6/2004 | Knowlton | |
| 6,751,507 B2 | 6/2004 | Morrison et al. | |
| 6,772,013 B1 | 8/2004 | Ingle et al. | |
| 6,776,779 B1 | 8/2004 | Roy et al. | |
| 6,830,052 B2 | 12/2004 | Carter et al. | |
| 6,836,688 B2 | 12/2004 | Ingle et al. | |
| 6,840,954 B2 | 1/2005 | Dietz et al. | |
| 6,852,110 B2 | 2/2005 | Roy et al. | |
| 6,875,209 B2 * | 4/2005 | Zvuloni et al. | 606/21 |
| 6,879,858 B1 | 4/2005 | Adams | |
| 6,882,885 B2 | 4/2005 | Levy et al. | |
| 6,889,090 B2 | 5/2005 | Kreindel | |
| 6,976,492 B2 | 12/2005 | Ingle et al. | |
| 7,004,942 B2 | 2/2006 | Laird et al. | |
| 7,022,121 B2 | 4/2006 | Stern et al. | |
| 7,141,049 B2 | 11/2006 | Stern et al. | |
| 7,238,183 B2 | 7/2007 | Kreindel | |
| 7,294,127 B2 | 11/2007 | Leung et al. | |
| 7,998,137 B2 | 8/2011 | Elkins et al. | |
| 8,603,084 B2 * | 12/2013 | Fish et al. | 606/34 |
| 2002/0032441 A1 | 3/2002 | Ingle et al. | |
| 2002/0049483 A1 | 4/2002 | Knowlton | |
| 2002/0062142 A1 | 5/2002 | Knowlton | |
| 2002/0120260 A1 | 8/2002 | Morris et al. | |
| 2002/0151887 A1 | 10/2002 | Stern et al. | |
| 2002/0156471 A1 | 10/2002 | Stern et al. | |
| 2002/0183735 A1 | 12/2002 | Edwards et al. | |
| 2003/0028180 A1 | 2/2003 | Franco | |
| 2003/0097162 A1 | 5/2003 | Kreindel | |
| 2003/0120326 A1 | 6/2003 | Dietz et al. | |
| 2003/0130575 A1 | 7/2003 | Desai | |
| 2003/0139740 A1 | 7/2003 | Kreindel | |
| 2003/0139790 A1 | 7/2003 | Ingle et al. | |
| 2003/0144576 A1 | 7/2003 | Presthus et al. | |
| 2003/0178032 A1 | 9/2003 | Ingle et al. | |
| 2003/0195593 A1 | 10/2003 | Ingle et al. | |
| 2003/0195604 A1 | 10/2003 | Ingle et al. | |
| 2003/0199866 A1 | 10/2003 | Stern et al. | |
| 2003/0212393 A1 | 11/2003 | Knowlton et al. | |
| 2003/0216728 A1 | 11/2003 | Stern et al. | |
| 2003/0216729 A1 | 11/2003 | Marchitto et al. | |
| 2003/0220635 A1 | 11/2003 | Knowlton et al. | |
| 2003/0236487 A1 | 12/2003 | Knowlton | |
| 2004/0000316 A1 | 1/2004 | Knowlton et al. | |
| 2004/0002704 A1 | 1/2004 | Knowlton et al. | |
| 2004/0002705 A1 | 1/2004 | Knowlton et al. | |
| 2004/0030332 A1 | 2/2004 | Knowlton et al. | |
| 2004/0034346 A1 | 2/2004 | Stern et al. | |
| 2004/0034400 A1 | 2/2004 | Ingle et al. | |
| 2004/0049251 A1 | 3/2004 | Knowlton | |
| 2004/0102824 A1 | 5/2004 | Sharkey et al. | |
| 2004/0111087 A1 * | 6/2004 | Stern et al. | 606/41 |
| 2004/0111136 A1 | 6/2004 | Sharkey et al. | |
| 2004/0111137 A1 | 6/2004 | Shankey et al. | |

(56) References Cited

U.S. PATENT DOCUMENTS

| | | |
|---|---|---|
| 2004/0127895 A1 | 7/2004 | Flock et al. |
| 2004/0172291 A1 | 9/2004 | Knowlton |
| 2004/0186535 A1 | 9/2004 | Knowlton |
| 2004/0193238 A1 | 9/2004 | Mosher et al. |
| 2004/0206365 A1* | 10/2004 | Knowlton .................. 128/898 |
| 2004/0210214 A1 | 10/2004 | Knowlton |
| 2004/0210282 A1 | 10/2004 | Flock et al. |
| 2004/0236177 A1 | 11/2004 | Matlock |
| 2004/0236393 A1 | 11/2004 | Ingle et al. |
| 2004/0249425 A1 | 12/2004 | Roy et al. |
| 2004/0260368 A1 | 12/2004 | Ingle et al. |
| 2004/0267336 A1 | 12/2004 | Morrison et al. |
| 2005/0154433 A1 | 7/2005 | Levy, Jr. et al. |
| 2005/0171582 A1 | 8/2005 | Matlock |
| 2005/0171583 A1 | 8/2005 | Mosher et al. |
| 2005/0187599 A1 | 8/2005 | Sharkey et al. |
| 2005/0203399 A1 | 9/2005 | Vaezy et al. |
| 2005/0288544 A9 | 12/2005 | Matlock |
| 2005/0288680 A1 | 12/2005 | Ingle et al. |
| 2006/0025837 A1 | 2/2006 | Stern et al. |
| 2006/0047331 A1 | 3/2006 | Lax et al. |
| 2006/0167533 A1 | 7/2006 | Spraker et al. |
| 2007/0078502 A1 | 4/2007 | Weber et al. |
| 2007/0083247 A1 | 4/2007 | Wyeth et al. |
| 2007/0088413 A1 | 4/2007 | Weber et al. |
| 2007/0093807 A1 | 4/2007 | Baxter et al. |
| 2007/0106349 A1 | 5/2007 | Karni et al. |
| 2007/0233191 A1* | 10/2007 | Parmer .............................. 607/1 |
| 2011/0178584 A1 | 7/2011 | Parmer et al. |

FOREIGN PATENT DOCUMENTS

| | | |
|---|---|---|
| JP | H11-504828 | 5/1999 |
| JP | 2002-238919 | 8/2002 |
| JP | 2003503118 | 1/2003 |
| JP | 2006-187668 | 7/2006 |
| WO | WO95/10981 A1 | 4/1995 |
| WO | WO96/22739 A1 | 8/1996 |
| WO | WO97/34534 A1 | 9/1997 |
| WO | WO98/19613 A1 | 5/1998 |
| WO | WO99/08614 A1 | 2/1999 |
| WO | WO99/53853 A1 | 10/1999 |
| WO | WO01/80723 A2 | 11/2001 |
| WO | WO03/011158 A1 | 2/2003 |
| WO | WO03/053355 A2 | 7/2003 |
| WO | WO2006/033067 A2 | 3/2006 |
| WO | WO2006/034357 A2 | 3/2006 |
| WO | WO 2006/105121 A2 | 10/2006 |

OTHER PUBLICATIONS

Parmer; U.S. Appl. No. 14/629,186 entitled "Vaginal remodeling device and methods," filed Feb. 23, 2015.

* cited by examiner

VAGINAL REMODELING DEVICE AND METHODS

RELATED APPLICATIONS

This patent application claims priority to U.S. Provisional Patent Application No. 61/243,686, filed on Sep. 18, 2009, titled "VAGINAL REMODELING DEVICE AND METHODS."

This patent application may also be related to pending U.S. patent application Ser. No. 11/704,067, filed on Feb. 7, 2007, titled "VAGINAL REMODELING DEVICE AND METHODS," which claims priority to U.S. Provisional Patent Application No. 60/743,247, filed on Feb. 7, 2006, entitled "VAGINAL REJUVENATION TREATMENT DEVICE AND METHODS." The disclosures of all of these patent applications are herein incorporated by reference in their entirety.

INCORPORATION BY REFERENCE

As a general matter, all publications and patent applications identified herein are incorporated by reference in their entirety to the same extent as if each individual publication or patent application was specifically and individually indicated to be incorporated by reference.

FIELD OF THE INVENTION

This invention relates generally to methods, devices and systems for remodeling tissue of the vagina and vulva, such as by the application of radiant energy.

BACKGROUND

The vagina is made up of three layers: a mucosa of stratified squamous epithelial tissue; the submucosa or lamina propria, containing vascularized connective tissue; and a deeper muscularis, containing smooth muscle. Collagen molecules are produced by cells resident in these tissues which synthesize three polypeptide chains that wrap around one another to form a triple helix. Collagen is a major type of fibrous protein that is a basic structural element of connective tissue, tendon, cartilage, and bone. Each of the collagen chains is approximately 1000 amino acid units in length, with glycine recurring regularly every third unit, and with proline and hydroxyproline recurring very frequently. Cross-linking occurs between the sides, not the ends, of collagen molecules and is coupled with the amino acid composition to give collagen its great strength. Collagen tissue tightening takes place in a direction parallel to an axis of collagen fibers.

The phenomenon of thermal contraction of collagen begins with a denaturation of the triple helix of the collagen molecule. Partial denaturation of collagen tissue results in a contraction of the collagen-rich spaces and provides a "tightening" effect on the overlaying tissue. Patents relevant to aspects of collagen denaturation and exploitation of this for medical or cosmetic purposes include U.S. Pat. No. 5,919, 219 to Knowlton for "Method for Controlled Contraction of Collagen Tissue Using RF Energy" and U.S. Pat. No. 5,755, 753 to Knowlton for "Method for Controlled Contraction of Collagen Tissue"; and U.S. Pat. No. 5,143,063 to Fellner for "Method of Removing Adipose Tissue."

Further patents and published patent applications include U.S. Pat. No. 6,350,276 to Knowlton for "Tissue Remodeling Apparatus Containing Cooling Fluid"; U.S. Pat. No. 6,387, 380 to Knowlton for "Apparatus for Controlled Contraction of Collagen Tissue"; U.S. Pat. No. 6,425,912 to Knowlton for "Method and Apparatus for Modifying Skin Surface and Soft Tissue Structure"; U.S. Pat. No. 6,453,202 to Knowlton for "Apparatus for Tissue Remodeling"; U.S. Pub 2002/0049483 to Knowlton for "Fluid Delivery Apparatus"; U.S. Pub 2003/ 0212393 to Knowlton for "hand piece with RD Electrode and Non-Volatile Memory"; U.S. Pub 2003/0236487 to Knowlton for "Method for Treatment of Tissue with Feedback"; and U.S. Pub 2004/0000316 to Knowlton for "Methods for Creating Tissue Effect Utilizing Electromagnetic Energy and a Reverse Thermal Gradient".

The vaginal tissue of women is stretched during vaginal child birth; at least some of the effects of the stretching are permanent and many women have long term medical consequences. Some consequences include physical problems, such as uterine prolapse, cystoceles, urethroceles, enteroceles, rectoceles, stress urinary incontinence, bowel movement problems, for which surgical options are available. Some consequences may include sexual aspects, as may follow from excessive loosening of the vagina and its opening, the introitus. Such loosening typically occurs with the first vaginal delivery, and the loosening tends to increase with subsequent vaginal deliveries. This effective of looseness in this region may include decreased pressure and friction during intercourse, and as a consequence, decreased sexual pleasure for women and their conjugal partners. Some surgical options can be exercised in an attempt to alleviate these problems, but surgical approaches can bring with them a risk of scarring that is entirely counterproductive with regard to the desired result. More generally, these surgical approaches are not highly popular because of the risks associated with an invasive procedure, in a sensitive area, especially when such procedures are considered medically optional.

Known systems and devices for treating the vagina are less than optimal, including those using radiant energy to modify the collagen. In particular, known systems are not optimized for the manipulation of the device, including the energy applicator (e.g., handle, applicator, etc.) and the cooling of the treated tissue. In addition, existing systems may not regulate the contact with the patient's tissue optimally. Finally, known systems have not proven to be simple to use, lightweight, and intuitive. Described herein are systems, devices, and methods of using them to remodel and treat the mucosal surfaces of the vagina, introitus, and vulva.

Thus, there is a need for effective approaches to treating a loose vagina and introitus with a non-invasive procedure, and particularly for systems and device that simplify and improve the treatment, particularly when applying RF energy. Accordingly, one object of the present invention is to provide systems (including apparatus and devices) and methods for corrective or restorative remodeling of the mucosal surfaces of the vagina, introitus, and vulva.

SUMMARY OF THE INVENTION

Described herein are devices and systems for remodeling target tissues, including the lamina propria and the muscularis, underlying the mucosal epithelium of a female genital tissue, and methods for remodeling tissue using these devices and systems. One such devices typically includes a hand piece and a treatment tip, and may form part of a system including the device, a source of coolant, and an electronic (e.g., control) system for control of the hand piece and tip, as well as a power source. Embodiments of the treatment tip may include a connector portion, which connects the tip to the hand piece, a midsection (which may be narrowed), and a distal portion that includes an energy delivery element. The treatment tip may also include a lumen or housing that defines an internal space. The internal space typically accommodates a cooling system, with a lumen for conveying a coolant (e.g., a refrigerating fluid), and applicators (e.g., nozzles) which are adapted to spray coolant on to the internal side of the energy delivery element thereby cooling it, such the cooled, in turn, cooling a genital mucosal epithelial surface on contact. The device may also include a coolant removal line for removing or venting the coolant.

The devices described herein may be configured to mate with a handle (hand piece). The handle may be elongate so that it may be gripped and manipulated along the same axis as the tip, for insertion in to the vaginal region. The handle may be adapted to include quick-release couplings for the tip distally (e.g., electrical couplings, coolant in-line couplings, coolant out-line couplings, sensor couplings, etc.). The proximal end of the handle may include a cord, cable, or other connector for connection to controller and/or power supply. In some variations, the handle is configured for gripping with both hands (e.g., two hands). The handle may also be configured so that it does not include a control (switch, button, etc.) to activate delivery of RF energy; instead, the delivery of RF energy may be delivered by a foot switch or other hands-free switch. This may enhance ease of handling of the applicator even as it is rotated and repositioned to reach target tissue within the body.

The system may also be configured so that the coolant is vented a substantial distance from the patient (e.g., away from the handle, at the end of the cord/cable). In some variations, the coolant is connected to a recycler for recycling or disposal; in other variations, the coolant is vented externally.

The energy delivery element may be configured as a radiofrequency, microwave, or ultrasound delivery element. Some particular embodiments include capacitively coupled RF electrodes, which may by monopolar or bipolar. Monopolar RF electrode-based embodiments may comprise a conductive pad to serve as a return electrode. Bipolar RF-based embodiments may include one or more pairs of electrodes. The electrodes may further comprise thermal sensors that provide feedback control based on local temperature, and may further comprise EEROM chips that identify the treatment tip type or convey configuration parameters of the electrode to the hand piece, or to the larger electronic system.

The energy delivery element and the treatment tip may also be adapted optimize contact with the genital epithelial surface, when contact and capacitive coupling is occurring between the tip and an epithelial contact site. Optimal contact may refer to a contact that optimizes the delivery of energy into the target tissue so that it is broadly uniform across the surface of the contact site, preferably without significant distortion along the edges of the contact site. Non-uniform delivery of energy does not serve the remodeling process well, and further may risk damage to the mucosal epithelium. These adaptive configurations may include a side mounted configuration of the energy delivery element, the face of the energy delivery element being substantially parallel with respect to the linear axis of the treatment tip. Other adaptive configurations may include a narrowed mid-section of the tip proximal to the distal portion. This configuration may allow the energy delivery element at the distal portion of the tip to project outward or forward from its surrounding support structure, thereby allowing the contact between the energy delivery element and the mucosal epithelium to be more accurate, deliberate, and visible, and for the level of contacting pressure to be better controlled by the physician.

The dimensions and configuration of the energy delivery element may be adapted to the optimize contact, particularly with the vaginal wall. The width of the energy delivery element is between 0.75 and 1.25 cm. Such a width is sufficient to engage the curved wall of the vagina in a manner that is sufficiently flat and parallel that the quality of contact across the face of the energy delivery element is substantially equal, without increased pressure, closer contact, or distortion along the edges of the element. Such a close contact allows for a uniform delivery of energy into the underlying target tissue. In some embodiments, the face of the energy delivery element is radially curved (with respect to the longitudinal axis of the tip) within the width of the element so as to create an arc of up to 30 degrees. Such curvature is also adapted to make parallel contact with the vaginal wall. An element of about 1 cm width, per embodiments of the invention, requires about 10 contact sites to radially treat a 300 degree arc inside a vagina, thus a 30 degree arc provides for a good fit against the curve of the vaginal wall and thereby provides a uniform delivery of energy into the target tissue.

In typical embodiments, the length of the energy delivery element is about 1 to about 3 cm in length; in other embodiments it may be as long as about 4 cm. This is a length well adapted to treating the lower aspect of the vagina, wherein treatment by the method comprises contacting the vaginal epithelium in a region that extends from the introitus inward to a position about 3 to 4 cm inward from the introitus. In some embodiments of the invention, the method can by practiced with a single row of parallel contact sites immediately inside the introitus. In other embodiments, the method may include deeper rows, or rows that overlap an initial row, while keeping the contact sites within the lower portion of the vagina.

In general, the energy-delivering tip of the device is cooled. The tip may be internally cooled; for example, a housing (cavity) within the tip may be cooled to cool the applicator tip. Cooling may be performed by application of a coolant (e.g., refrigerant) within the housing. For example, the housing may be cooled by spraying a refrigerant from one or more nozzles within the housing against the back size (internal side) of the energy delivery surface. The pattern of sprayed coolant may be optimized. It is desirable to the applicator completely and quickly in a highly controllable fashion. Controlling the temperature of the applicator tip allows the applied energy to be controlled, since the tissue temperature may also be regulated. Rapid cooling is preferable so that the device may be used efficiently and speedily. However, it is also beneficial to conserve coolant, and to control the path of coolant so as to allow most efficient use of the hand held applicator. Thus, described herein are devices configured to balance the conservation of coolant with quick and thorough cooling of the applicator. For example, the devices may be configured to have a plurality of nozzles having a spray pattern that covers the majority of one side of the applicator surface (e.g., energy delivery surface). The number of nozzles may be minimized while maximizing the distribution of the spray pattern within the internal tip space. In addition, the applicator tip and handle region may include a coolant delivery channel and a coolant return channel that include one or more seals and quick-connect/quick-release connectors. The hand-held region may also include one or more coolant delivery channels and coolant return channels that mate with the tip coolant delivery and coolant return channels. The coolant return pathway may extend proximally through the device and may vent to a release site that is located proximally from the patient. For cample, the coolant return channel may extend through the cabling or connector at the proximal end of the applicator for proximal venting. In some variations the coolant return channel couples with a coolant recycler for capture of the coolant. The coolant recycler may be configured to collect the coolant for later re-use and/or disposal, or it may include coolant recycling components (e.g. compressors, etc.).

The handle and tip (applicator) may also include one or more lights. The lights (e.g., indicator lights) may help guide operation of the device, including attachment of the tip, alignment of the device, alignment of the tip with the handle, etc. For example, in some variations the handle includes a light encircling the proximal or distal end of the device that may indicate the orientation of the handle. In some variations, the indicator lights may indicate that the tip is secured to the handle, and/or the status of the tip (cooled and ready for use, etc.). The handle may include one or more controls, such as a button or switch, for operating the device to apply energy from the energy delivery element.

As mentioned, the tip may be configured to be quickly connected and/or replaced on the handle. Thus, the tip and the handle region may be modular. In some variations, the tip and handle are integrally (e.g. permanently) connected. In other variations, the tip may be replaced between procedures while the same handle is reused. Thus, the tip and handle may be adapted for quick and accurate connection. Thus, the tip may include an electrical connector for connecting to a complementary connector on the handle for powering the energy delivery element. The tip and handle may also include sealing connectors for connecting coolant delivery and return lines. The connectors may be snap-fit (e.g., friction fits) that may be securely attached and later removed. The tip may be keyed to the handle so that it can attach only in the proper orientation or configuration. In some variations the device may include an indicator that indicates when the tip is properly attached (e.g., so that the coolant lines are sealed, etc.).

Also described are methods for remodeling a therapeutic zone of tissue within a target tissue of female genitalia. The target tissue lies immediately beneath the mucosal epithelium of genital tissues, and includes the lamina propria, a connective tissue that includes collagen in the extracellular space, and the muscularis, which includes smooth muscle. The target zone of embodiments of the invention does not include deeper tissue, such as endopelvic fascia.

The anatomical areas of the female genitalia treated by embodiment of the invention include the vulva and the vagina, and the introitus, the opening of the vagina. The vulva includes tissue radiating outward from the introitus to Hart's line, where mucosal epithelium gives way to skin on the outer surface of the labia minora. With more specific regard to the vagina, embodiments of the method comprise treating the lower portion of the vagina, a portion extending from the introitus to a location from about 2 cm to about 4 cm inward from the introitus, in other embodiments the location may extends inward as far as about 6 cm. With regard to the circumference of the inner wall of the vagina, a clock-position reference scheme is helpful. The urethra lies next to the anterior wall of the vagina, the location of the vaginal wall nearest the urethra and urethral opening may be considered 12 o'clock. With this reference point, the target tissue of embodiments of the invention includes the approximately 300 degree arc between 1 o'clock and 11 o'clock. Embodiments of the invention do not include treating the approximately 60 degree arc between 11 o'clock and 1 o'clock because the practice of this invention is not directed toward tissue in the vicinity of the urethra.

Embodiments of the method include heating the target zone with radiant energy, typically radiofrequency (RF) energy, but other embodiments may use microwave or ultrasound energy. The method includes contacting the mucosal epithelium with a treatment tip that has an energy delivering element and a cooling mechanism. By delivering energy to the tissue while cooling the epithelial surface, a reverse thermal gradient may be created. The RF energy penetrates through the cooled epithelium and into the underlying target tissue, and heats the tissue.

A zone of tissue that is heated within the target tissues to a threshold level, i.e., to a therapeutic temperature that causes remodeling is termed a therapeutic zone. Not all tissue within the target tissue necessarily reaches this threshold level of heat. In some cases, cooling from the treatment tip may penetrate into the target tissue, and in this situation, the presence of cooled tissue may have an effect on the therapeutic zone, by moving it deeper within the target tissue, for example, or by constraining its volume.

Energy delivered from the treatment tip may heat the target tissue to a temperature as high as about 80° C. In some embodiments, therapeutic temperature may range between about 45° C. and about 80° C. In other embodiments, the therapeutic temperature may range between about 50° C. and about 75° C. In still other embodiments, the therapeutic temperature may range between about 55° C. and about 70° C. Heating may be subject to feedback control during a treatment procedure, so as to keep the temperature within a predetermined temperature range. Feedback may be provided by one or more sensors, including thermal sensors (e.g., thermisters) and impedance monitors. The treatment tip may cool the epithelium to a temperature between about 0° C. and about 10° C. A reverse thermal gradient, accordingly may be represented a low temperature of between about 0° C. and about 10° C. at the mucosal epithelium, and a high temperature of between 45° C. and about 80° C. in the target tissue. During a typical procedure, according to embodiments of the invention, any period of heating is accompanied by cooling; however cooling may also precede heating, and follow heating.

Methods of treatment comprise contacting the treatment tip to a contact site on the mucosal epithelium. The contact site conforms to the dimensions of the treating surface of the treatment tip. During the course of a single treatment, as for example would occur to a visit to a medical office, typically a plurality of contact sites may be treated. During a procedure, a single contact site may be contacted multiple times. The summed total of mucosal contact sites comprises a treatment area. Such an area, comprising multiple contact sites may be recorded on a grid. The method may be applied on more than one occasion; a patient may return to her physician at a later date when the effects of a previous treatment may be evaluated and a treatment repeated. The treatment areas of the separate procedures may be the same, be different, or overlap.

Remodeling genital tissue, per embodiments of the invention may include heat-denaturing collagen within collagen-rich areas in the target tissues. Inasmuch as the overlaying mucosal epithelium is cooled by the method, it does not get heated, and is substantially unaffected by the method. Remodeling of target tissue within the therapeutic zone may occur substantially during the time when the tissue is being heated. Remodeling may also occur substantially after the heating has occurred, for example days or weeks later. Such remodeling comprises biological healing responses to the stress of heating, and such responses may include the deposition of new collagen. Whether by denaturation of existing collagen, or by later deposition of new collagen, the effect of remodeling on the tissue is generally one of tissue contraction or tightening. Thus, embodiments of invention comprise tightening the vagina and the introitus. The effect of vaginal childbirth on the vagina and introitus is a loosening of these tissues. Inasmuch as the method comprises tightening these tissues, the method has a rejuvenating effect in that it remodels the tissue toward the conformation it had prior to having experienced vaginal childbirth.

For example, described herein are apparatus for remodeling a therapeutic zone within tissue underlying a mucosal epithelium of female genital tissue. An apparatus may include: an elongate handle configured to be held within two hands; and a treatment tip configured to be removably coupled to the elongate handle. The tip may include: a shaft comprising a longitudinal axis: an energy delivery element having an epithelium-contacting surface: and an internal cooling chamber configured to internally cool the energy delivery element, wherein the energy delivery element comprises a thermally-conductive surface that is adapted to allow cooling of the epithelium while transmitting RF energy to heat the target tissue.

As mentioned above, the energy delivery element may be configured to be substantially parallel to the longitudinal axis of the shaft. The energy delivery element may be configured to have a width of about 0.75 cm to about 1.25 cm, and/or may have a length of about 1 cm to about 3 cm. The energy delivery element may be substantially flat.

In some variations, the internal cooling chamber comprises a plurality of coolant nozzles configured to spray cooling fluid on an internal portion of the energy delivery element. For example, the apparatus may have three coolant nozzles. The energy delivery element may have at least one RF electrode (e.g., four electrodes). The apparatus may also include at least one temperature sensor located in close proximity to the energy delivery element. The temperature sensor may be a thermister, for example.

The apparatus may also include return coolant pathway extending proximally from the elongate handle configured to channel the used coolant away from a patient.

In some variations the apparatus includes a flat cable connecting the handle to the integrated controller. The cable may include a coolant delivery channel and a coolant return channel, at least one RF power line.

The handle may not include a button or switch controlling the application of RF energy. Instead, the application of RF energy may be controlled by a hands-free mechanism (e.g., foot switch, voice activation, etc.) or automatically by a controller, or the like. For example, the handle may be configured to automatically stimulate after adequate contact with the tissue has been sustained for a predetermined time period.

Also described herein are systems for remodeling a therapeutic zone within tissue underlying a mucosal epithelium of female genital tissue, the system comprising: an elongate handle configured to be held within two hands, wherein the handle extends in a longitudinal direction; a treatment tip configured to be removably coupled to the elongate handle (the tip comprising: a plurality of energy-delivery elements having epithelium-contacting surfaces, and at least one internal cooling chamber configured to internally cool the energy delivery elements, wherein the energy delivery element comprises a thermally-conductive surface that is adapted to allow cooling of the epithelium while transmitting RF energy to heat the target tissue); and an integrated controller. The integrated controller may include: a housing; an RF generator within the housing; a cooling sub-system within the housing; and a controller for controlling operation of the treatment tip and determining when the treatment tip is in contact with a target tissue.

The system may also include a flat cable connecting the handle to the integrated controller, the cable including a coolant delivery channel and a coolant return channel, at least one RF power line. In some variations the system includes a foot switch configured to connect to the integrated controller and trigger the application of RF energy by the plurality of energy-driven elements.

The integrated controller may also include a display configured to display control information. The display may be configured to display a map of the plurality of energy-delivery elements indicating contact status.

In some variations, the integrated controller is portable. For example, the integrated system may weigh less than fifty pounds, and/or have a footprint that is less than 25 inches by 15 inches by 16 inches (e.g., 23 inches deep, 15 inches high, and 16 inches wide).

Also described herein are methods of determining if an energy-delivery element of a treatment tip for an RF energy device is in adequate communication with a tissue to be treated, without determining an electrical impedance from the tissue. For example, the method may include the steps of: determining the time since the energy-delivery element of the treatment tip was last activated; taking the temperature of one or more sites on the treatment tip; determining if the energy-delivery element is in contact with the tissue without applying RF energy to the tissue by comparing the temperature of the one or more sites on the treatment tip to a threshold function for the time since the treatment tip was last activated; and indicating if the treatment energy-delivery element is in contact with the tissue.

In some variations the step of comparing the temperature of the one or more sites on the treatment tip to a threshold function comprises comparing to a threshold function having a ramping temperature threshold from about 30 to about 180 seconds since the energy-delivery element of the treatment tip was last activated. For example, the treatment threshold may ramp from about 18 degrees Celsius to a temperature just under body temperature between a finite time range (e.g., between about 30 seconds and about 180 seconds) since the energy-delivery element of the treatment tip was last activated. In one variation, the treatment threshold ramps from about 18 degrees Celsius to about 27 degrees Celsius between a finite time range since the energy-delivery element of the treatment tip was last activated.

Also described herein are methods for remodeling a therapeutic zone within a target tissue underlying a mucosal epithelium of female genital tissue. The methods may include: cooling a disposable treatment tip of an applicator from an internal lumen in the applicator, wherein the disposable treatment tip includes one or more atraumatic energy-delivery elements; heating the target tissue using the treatment tip; and remodeling the therapeutic zone of target tissue.

The method may also include confirming contact with the tissue and the one or more energy-delivery elements based on the temperature of a portion of the treatment tip on or near the one or more energy-delivery elements and the time since the treatment tip was last activated. For example, the step of confirming contact comprises confirming contact without applying energy. Any of the previously described method steps may also be included or applied to this method.

BRIEF DESCRIPTION OF THE DRAWINGS

FIG. 6A shows an electrode with a flat surface, and FIG. 6B shows an electrode with a curved surface.

DETAILED DESCRIPTION OF THE INVENTION

Apparatus

Figure 1:
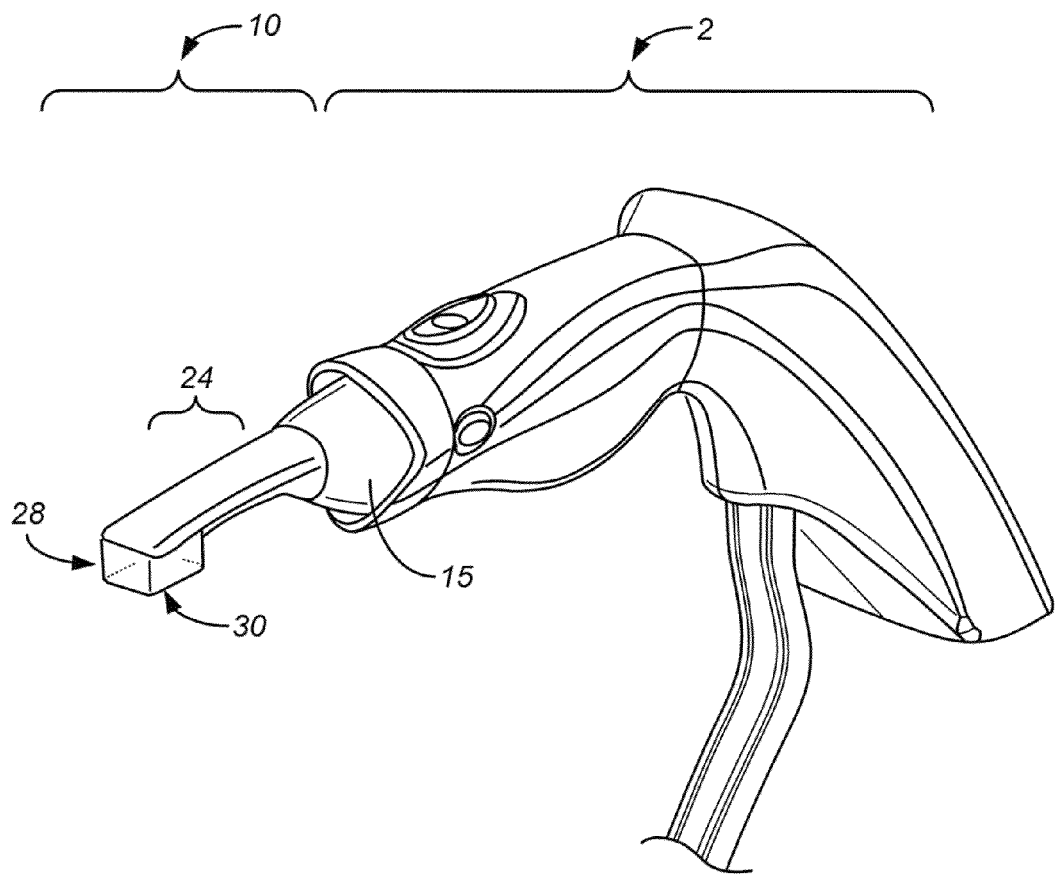
FIG. 1 is a perspective view of an apparatus for applying radiant energy to the target tissue while cooling the epithelium in order to remodel genital tissue, shown are a hand piece and a connected treatment tip.

Embodiments of the present invention include an apparatus and method for remodeling female genital tissue by applying heat to a target tissue underlying the surface mucosal epithelium, while cooling the surface epithelium itself. The apparatus and methods may build on those of prior art such as those described by Knowlton, including US 2004/0000316, and others cited in the background, all incorporated by this reference, but include novel features in the apparatus and methods that are configured and adapted to particulars of the female genital treatment site, the mucosal epithelium contacted by the present apparatus, and the underlying target tissue that is remodeled according to aspects of the invention. FIG. 1 shows an apparatus 1, which comprises a hand piece 2 and a treatment tip 10. The hand piece 2 is adapted to be held by an operator, such as a physician, and may include connections to a larger supporting system (not shown), or, in some embodiments, it may be operable as self-sufficient independent device. FIG. 1 shows the connector portion 15 of the shaft of the treatment tip, the narrow midsection 24, and the distal portion 28, which includes the energy delivery element 30.

Figure 2:
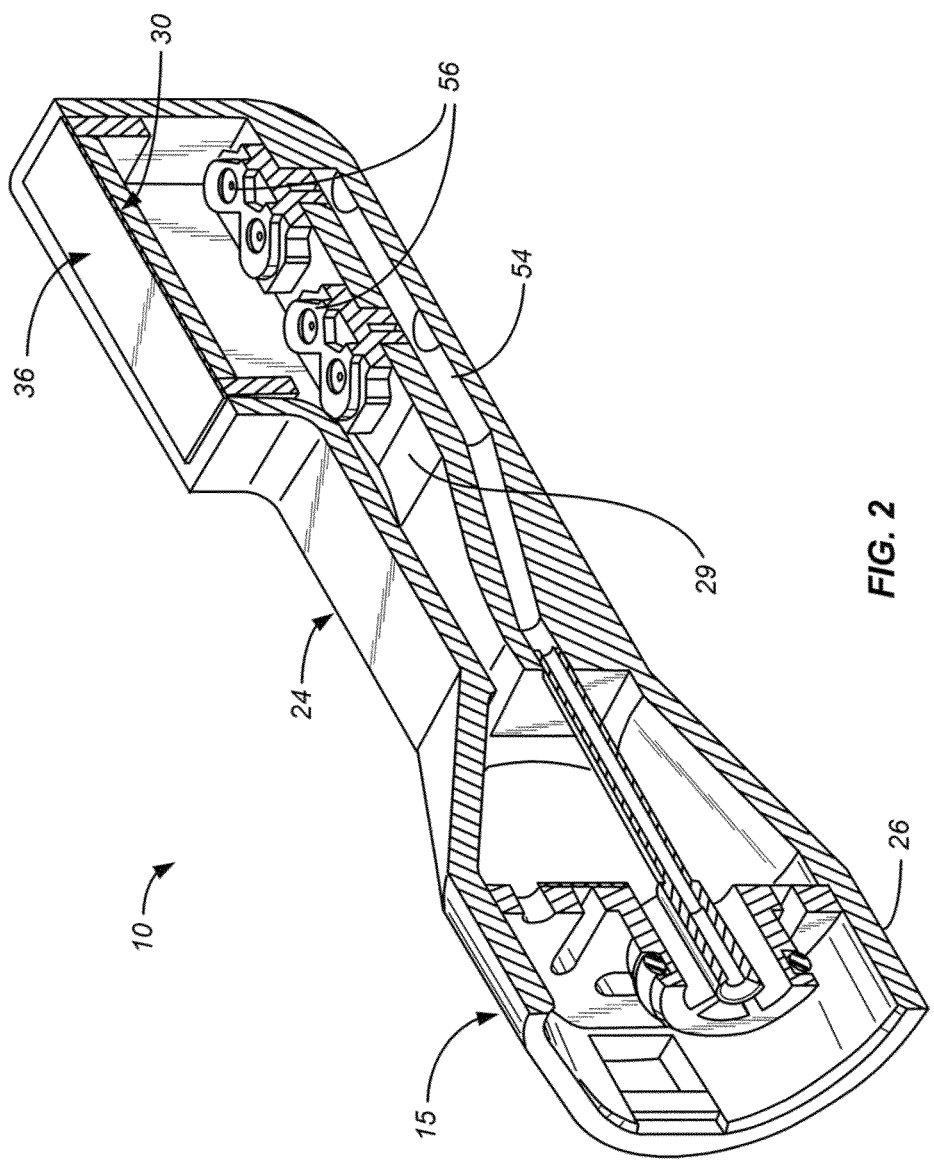
FIG. 2 is an exposed perspective view of a treatment tip embodiment.
Figure 3:
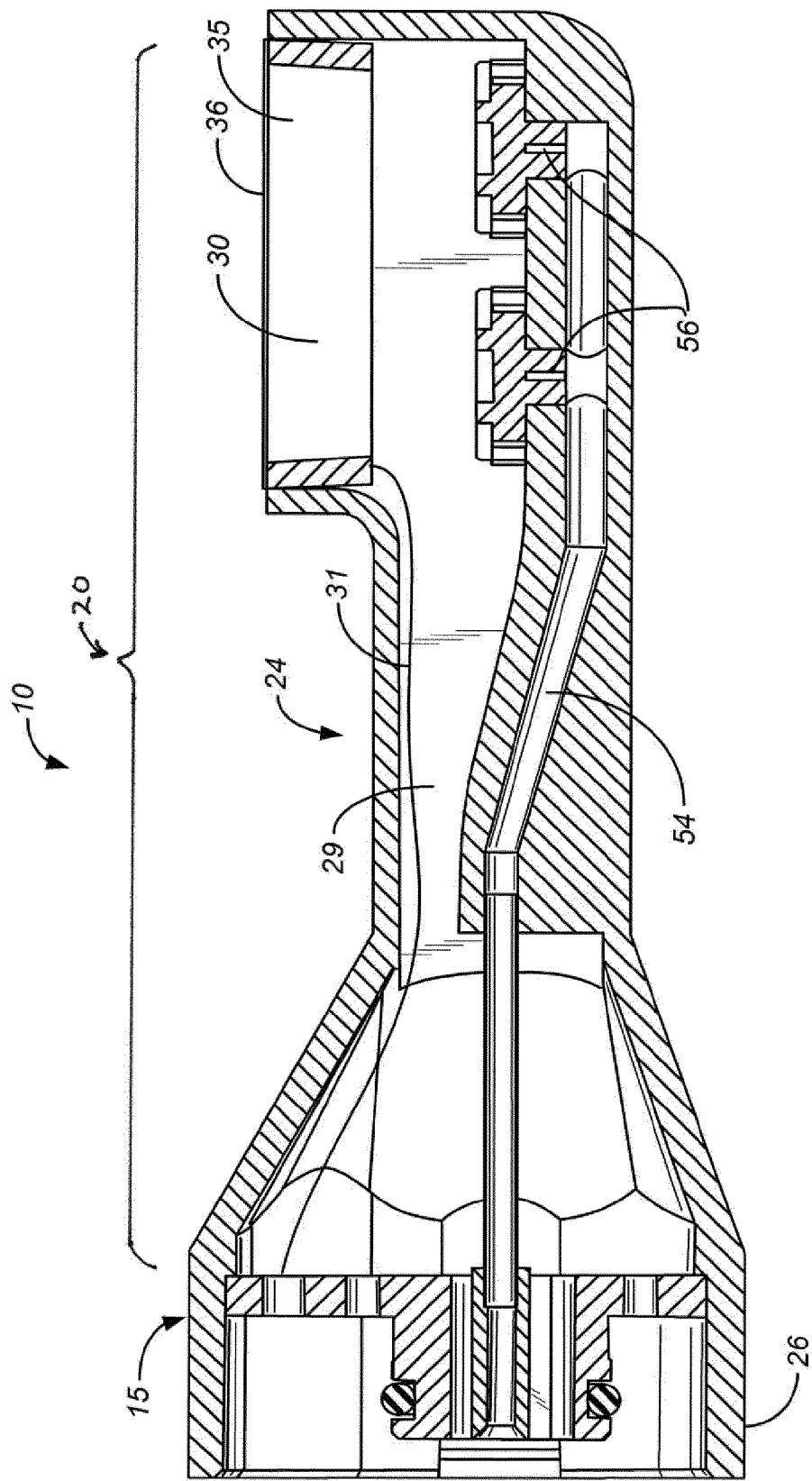
FIG. 3 is an exposed side view of a treatment tip embodiment.
Figure 4:
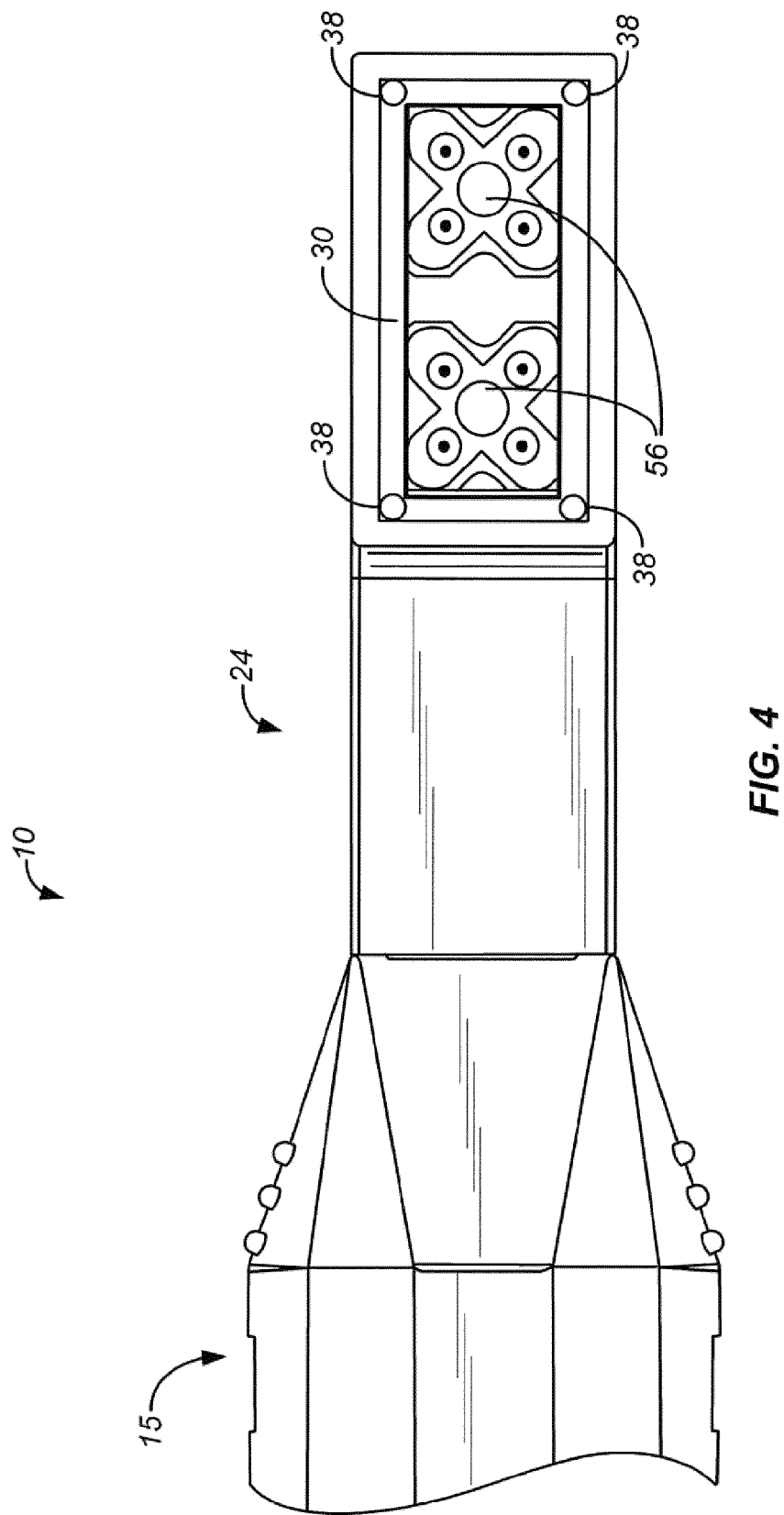
FIG. 4 is frontal cutaway view of the treatment tip, showing cooling nozzles that underlay the energy delivery element that contacts the epithelium

FIGS. 2-5 provide various views of the treatment tip. FIG. 2 provides an exposed view from a perspective proximal to the tip, FIG. 3 is an exposed view from a side perspective, and FIG. 4 is a frontal view directed toward the energy delivery element, exposed so as to reveal the nozzles directly below the energy delivery element. FIG. 5 shows embodiments of the treatment tip that vary with respect to the type of energy delivery element (i.e., radiofrequency electrodes, variously monopolar, a bipolar pair, and multiple bipolar pairs). The treatment tip 10, depicted in greater detail in FIGS. 2-5 includes a housing 26, a connector portion 15, and an energy delivery element 30, which receives input through wire 31 (FIG. 3). The treatment tip as a whole is designed as a quick connect/disconnect unit with respect to its attachment to the base hand piece 2. The connection of the treatment tip 10 to the hand piece 2 is by way of the connector portion 15 of the treatment tip. The housing 26 defines an interior space 29 which extends forward from the connector portion 15 to the distal end 28 of the treatment tip. The energy delivery element 30 is side-mounted with respect to the linear axis of the tip, configured to face outward on a side on the distal portion 28 of the tip. By a side-mount, or by mounted so as to face a side of the treatment tip, it is meant that the energy delivery element 30 is configured to be approximately parallel to the linear axis of the shaft 20.

Between the connector portion 15 and the distal portion 28 of the tip is narrowed mid-section mid-portion 24, such narrowing or tapering on the same side as that which the energy delivery element 30 faces (narrowing may occur generally in the midsection 24, but embodiments typically include the narrowing at least on the same side as the energy delivery element). The side-mounted configuration of the energy delivery element 30 and the tapered section 24 of the tip both are adapted to optimize the contact of the energy delivery element to the epithelial surfaces of the female genitalia, in particular to those of the vagina. Details of the female genitalia are described further below. For the purpose of describing the advantage of a side placement 22 and the tapered section 21 of the shaft, of the canal-like aspect of vagina and entry into it with an instrument that engages the side of the canal are considered. An elongate structure best suited for entry into the vagina, and to make a substantially flat or surface-to-surface parallel contact with the side of the vagina, a side mounted energy delivery unit is advantageous. An advantage conferred by parallel contact is that contact pressure is distributed equally across the contact area, with no pressure biased against any side of the contact site. With such a uniformly pressured contact occurring, so too is energy uniformly directed to underlying target tissue. The narrow mid-section 24 of the shaft further provides a functional advantage to the tip 10 in that it allows the energy delivery element 30 at the distal portion 28 of the tip to project forward from the body of the shaft, such projection allowing the physician operating the apparatus to make contact to epithelium with appropriate pressure, to make the contact more discrete, to make the contacting flat, and to better visualize the contact.

The overall length of the treatment tip 10 in this initial example, from the base of the connector portion 15 to the foremost point of the distal portion 28 is designed such that the side mounted energy delivery element 30 reaches the innermost region of the vagina that is treated by the tip. Accordingly, embodiments of the tip may have an overall length of between about 2.75 inches and 4.25 inches. Particular embodiments have an overall length of between about 3 inches and about 4 inches. Still more embodiments have an overall length of between about 3.25 inches and about 3.75 inches. This overall length is appropriate for providing the treatment tip access the lower portion of a gently unfolded vagina.

The energy delivery element 30 also has dimensions advantageously adapted to making appropriately flat contact with the vaginal wall. The width of the element, an RF electrode in typical embodiments, in some embodiments is between about 0.7 cm and about 1.3 cm. In other embodiments, the width is between about 0.8 cm and about 1.2 cm. In still other embodiments, the width is between about 0.9 cm and about 1.1 cm. In some embodiments, the length of the energy delivery element 30 is between about 2 and about 3 cm. In other embodiments, the length is between about 2.25 cm and about 2.75 cm. The constraints on the length are related to the advantageous aspect of being able to make contact at particular sites on the mucosal epithelium, to avoid contact with other sites, deeper in the vagina, where it is not desired to make contact, and generally to make contact discretely and efficiently at the desired treatment area. The method of treatment typically comprises treating the vagina at a point no deeper than about 3.5 cm in from the introitus. The constraints on the width of the energy delivery element related, as described above, to the desirability of being able to make a substantially flat contact with the inner aspect of a curved surface. By constraining the width of the contact site, an increased pressure or closeness of contact that could occur along lengthwise edges is minimized.

Figure 6A:
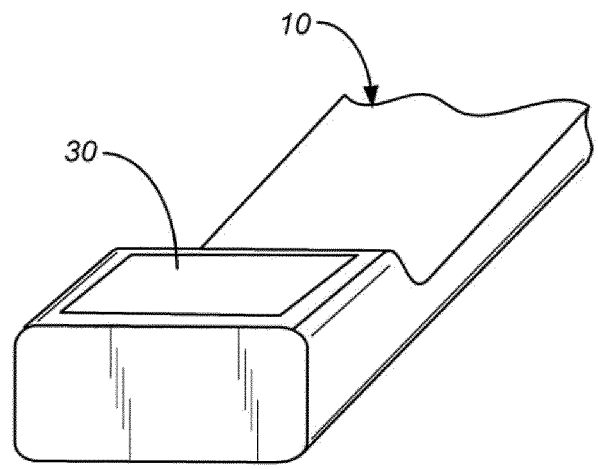
FIGS. 6A and 6B show front perspective views of two embodiments of a treatment tip, treatment side facing up, where
Figure 6B:
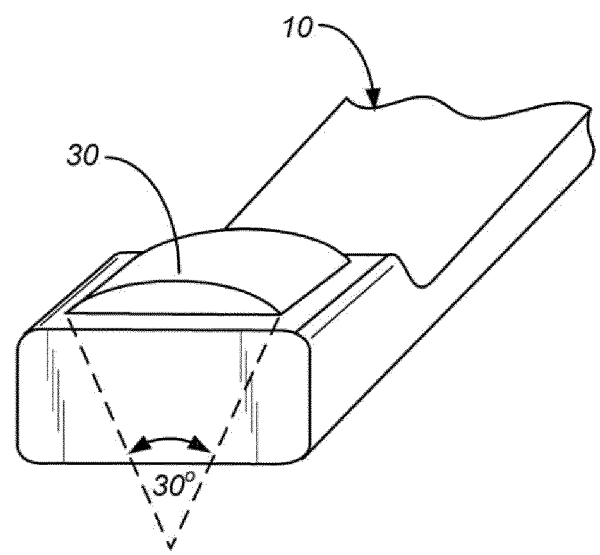

In embodiments depicted above, the energy delivery element has had a flat configuration. FIG. 6 shows another embodiment of the treatment tip 10, where the energy delivery element 30 takes a curvilinear form. In other embodiments the energy delivery element comprises a curved surface such it includes a curvature radially with respect to the linear axis while remaining parallel to the linear axis, the form representing an arc of a cylinder. FIG. 6A shows a treatment tip embodiment where the energy delivery element is flat, while the embodiment in FIG. 6B has a curved surface, the curve being radial with respect to the linear axis of the tip. The arc of the curvature may be as large as approximately 30 degrees. Some embodiments may include a curvature of about 30 degrees. The 30 degrees of curvature is adapted to fit the curvature of the vaginal wall.

Accordingly, various configurational and dimensional aspects of the treatment tip 10 and the energy delivery element 30 are advantageous for the method of remodeling genital tissue. These features are particularly suited for treating the vaginal wall, but also are appropriate for treating mucosal epithelial surfaces of female genitalia outside the vagina. As described above, these features include (1) the side-facing orientation of the energy delivery element with respect to the linear axis of the treatment tip and its shaft, (2) the overall length of the treatment tip from its proximal end to the distal end, (3) the narrow portion 24 of the tip which allows the energy delivery element to project forward from a background structure, rather than being in contiguous plane with surrounding structure, (4) the surface dimensions of the energy delivery element, particularly the width, which allow for substantially flat contact with the vaginal wall in the case of a flat energy delivery element 30, and (5) in the case of embodiment with a curved energy delivery element, a particularly close fit between the energy delivery element and the vaginal wall is achievable. All such enumerated features contribute to a uniformly-distributed contact between the energy delivery surface and the mucosal epithelium, such uniform fit diminishes the likelihood of edge-biased contact that could harm the epithelium, and affirmatively promotes uniform distribution of energy across the area of site where the energy delivery element contacts the epithelium and through which energy radiates into the underlying target tissue. Uniformity in flux across a surface area promotes an advantageous uniformity, consistency, and predictability in the remodeling response. Further, and equally important, small variation in flux also minimizes occurrence of damage, either to the epithelium or the target tissue, which can occur when large excursions in energy flux include, as they inevitably do, areas which receive high rates of energy flux.

As seen in FIGS. 2 and 3, the interior space 29 of the tip accommodates a cooling system to cool the energy delivery element, which comprises a cooling lumen 54 for conveying cooling fluid 52 to nozzles 56. The cooling fluid may comprise a refrigerant, such as 1,1,1,2-tetrafluoroethane (R 134A), which is stored in a reservoir (not shown) under pressure, and may be conveyed through a lumen 54 to nozzles 56. The nozzles are configured within the interior space (internal cooling chamber) 29 in the distal portion 28 or the tip 10 under the inner surface of the energy delivery element 30. On release of the refrigerant from the nozzles, it sprays onto the interior surface and cools the element as the refrigerant undergoes a liquid to gas transition. The exterior surface of the energy delivery element, when in contact with an epithelial mucosal surface as during the practice of method embodiments of the invention, cools the epithelial surface upon such contact. This surface cooling may prevent the buildup of heat on the mucosal surface, the energy being delivered by the delivery element passes through the mucosal surface and into the underlying tissue targeted by the invention, which is then heated. FIGS. 10A-10B and 12-14B, described in more detail below, illustrate cooling systems including coolant spray and the removal and/or re-cycling of coolant.

The energy delivery element 30 is may be any of an RF electrode, a microwave emitter, or an ultrasound emitter. Embodiments that include an RF electrode will be described in some detail. The RF electrode, in some embodiments, is a capacitive electrode, which capacitively couples to the mucosal epithelium. The RF electrode, without limiting the scope of the invention, may have a thickness in the range of about 0.01 to about 1.0 mm.

The RF electrode 30 has a conductive portion 35 facing the interior space 29 within the treatment tip, and a dielectric portion 36 facing the exterior of the tip. Conductive portion 35 may comprise a metal, exemplary metals including copper, gold, silver, and aluminum. Dielectric portion 36 may comprise a variety of different materials including, by way of example, polyimide, Teflon® and the like, silicon nitride, polysilanes, polysilazanes, polyimides, Kapton and other polymers, antenna dielectrics and other dielectric materials well known in the art. Other exemplary dielectric materials include polymers such as polyester, silicon, sapphire, diamond, zirconium-toughened alumina (ZTA), alumina and the like. Dielectric portion 36 covers the conductive portion 35, and is disposed between conductive portion 35 and the patient's tissue during treatment. In another embodiment, RF electrode 30 is made of a composite material, including but not limited to gold-plated copper, copper-polyimide, silicon/silicon-nitride and the like. In one embodiment, conductive portion 35 adheres to dielectric portion 36 which can be a substrate with a thickness, by way of example and without limitation, of about 0.001". This embodiment is similar to a standard flex circuit board material commercially available in the electronics industry. In this embodiment, dielectric portion 36 is in contact with the mucosal epithelium, and the conductive portion 35 is separated from the mucosal epithelium.

Figure 5A:
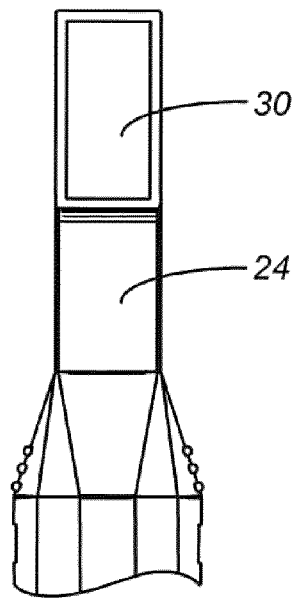
FIG. 5 shows frontal views of the treatment tip embodiments with (A) a single monopolar electrode, (B) a single bipolar of electrodes, and (C) multiple pairs of bipolar electrodes.
Figure 5B:
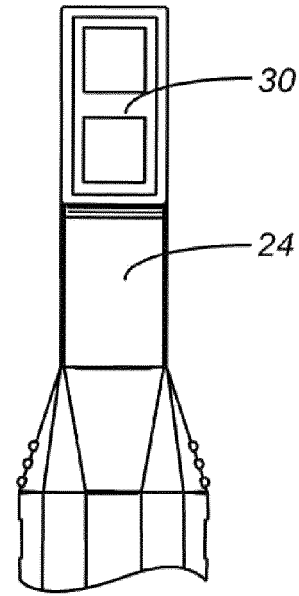
Figure 5C:
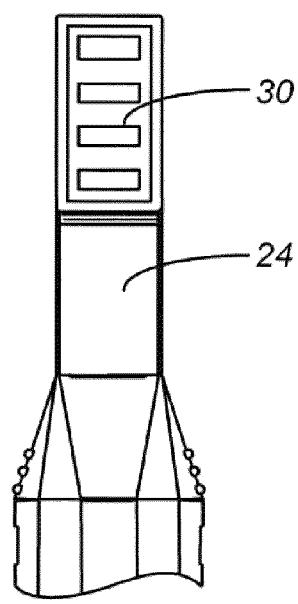

Generally, RF electrodes 30 can be either monopolar or bipolar. In the monopolar mode, RF current flows through body tissue from a return electrode which can be in a form of a conductive pad applied to another portion of the patient's body. FIG. 5 shows various embodiments of electrodes from a facing perspective, for example FIG. 5A shows a tip with a monopolar pair of electrodes, FIG. 5B shows a bipolar pair, and FIG. 5C shows a tip with multiple bipolar pairs. Additionally, the electrode may be equipped with an integrated EEROM (Electrically Erasable Read Only Memory, also known as EEPROM) programmable memory chip at any suitable location within the treatment tip (not shown). Such a chip may provide identifying information or other information about the operational status or configuration parameters of the RF electrode to the system, such parameters may include, by way of example, the type and size of the electrode, the number of times the energy delivery element has been fired, and the like. Additionally, thermisters (thermal sensors) 38 (shown in FIG. 4) may be provided at each corner of an RF electrode, or otherwise in close proximity to the electrode, to provide feedback to the system on the temperature at their location.

In some embodiments, the treatment tip as a whole is designed as a single-use disposable component, while the hand piece 2 is typically a reusable instrument. The single-use and disposable aspects of treatment tip 10 are in accord with its designated use in a single procedure, in the context of a female patient having a procedure, per embodiments of the method further described below, in a medical setting. Accordingly, the entirety of construction and components of the treatment tip retain their integrity through sterilization procedures, and the tip is typically packaged singly in a container or a wrap that preserves the sterile integrity of the tip until such time when it is unwrapped and connected to the hand piece 2 in preparation for a treatment procedure. Embodiments of the treatment tip 10 are modular in that they have a common connector portion 12 but may have variations in the shaft portion 20 and energy delivery elements 30 and cooling mechanism components, such as the fluid 52 or nozzles 56.

Electronic Support System for the Apparatus

The apparatus 1 may be included in a larger electronic system with features including a power source, such as an RF power source that provides energy to an RF power generator and power flows there from to RF electrodes 30. A multiplexer may measure current, voltage and temperature, at the thermal sensors 38 associated with to each RF electrode 30. The multiplexer may be driven by a controller, which can be a digital or analog controller, or a computer with software. When controller is a processor (such as a microprocessor of a computer) it can include a CPU coupled through a system bus. On the system there may also be a keyboard, disk drive, or other non volatile memory systems, a display, and other peripherals. Also coupled to the bus may be a program memory and a data memory.

An operator interface includes operator controls and a display. The controller can be coupled to different types of imaging systems including ultrasonic, thermal sensors 38, and impedance monitors 39. Current and voltage are used to calculate impedance. A diagnostic phase can be initially run to determine the level of treatment activity. This can be done through ultrasound as well as other means. Diagnostics can be performed both before and after treatment.

Thermal sensors 38 measure voltage and current as delivered to the desired treatment site; the output for these sensors is used by a controller to control the delivery of RF power, which can also control temperature and power. An operator set level of power and/or temperature may be determined to provide operating limits that will not be exceeded. The controller may maintain the set level under changing conditions. The amount of RF energy delivered may control the amount of power. A profile of power delivered can be incorporated in the controller, as well as a preset amount of energy to be delivered. Feedback control can be based on monitoring of impedance, temperature, or other indicators, and occurs either at the controller or at RF generator, if it incorporates a controller. For impedance measurement, this can typically be achieved by supplying a small amount of non therapeutic RF energy. Voltage and current are then measured to confirm electrical contact.

Circuitry, software and feedback to controller result in full process control and are used to change power, the duty cycle, monopolar or bipolar energy delivery, flow rate and pressure, and can also determine when the process is completed through time, temperature and/or impedance. These process variables can be controlled and varied in accordance with tissue temperature, as monitored at multiple sites on contacting exterior surface 34, as well as by monitoring impedance to current flow at each RF electrode 39, indicating changes in current carrying capability of the tissue during the process. Further, a controller can provide multiplexing, monitor circuit continuity, and determine which RF electrode 30 is activated.

Thermal sensors 38 can be thermistors, which have a resistance that varies with temperature. An analog amplifier can be a conventional differential amplifier circuit for use with thermistors and transducers. The output of the analog amplifier is sequentially connected by an analog multiplexer to the input of an analog digital converter. The output of the amplifier is a voltage, which represents the respective sensed temperatures. The digitized amplifier output voltages are supplied by analog to digital converter to a microprocessor, which calculates the temperature or impedance of the tissue. In some embodiments, the microprocessor can be a type 6800, however, any suitable microprocessor or general purpose digital or analog computer can be used to calculate impedance or temperature. The microprocessor sequentially receives and stores digital representations of impedance and temperature. Each digital value received by the microprocessor corresponds to different temperatures and impedances.

Calculated temperature and impedance values can be indicated on a display. Alternatively, or in addition to the numerical indication of temperature or impedance, calculated impedance or temperature values can be compared by the microprocessor with temperature and impedance limits. When the values exceed predetermined temperature or impedance values a warning can be given on the display and additionally, the delivery of RF energy to its respective electrode can be decreased or multiplexed to another electrode. A control signal from the microprocessor can reduce the power level by the RF generator, or de-energize the power delivered to any particular electrode. The controller receives and stores the digital values that represent temperatures and impedances sent. Calculated surface temperatures and impedances can be forwarded by the controller to the display. If desired, the calculated surface temperature of the vaginal mucosal tissue layer is compared with a temperature limit and a warning signal can be sent to the display. Similarly, a control signal can be sent to the RF power source when temperature or impedance values exceed a predetermined level.

Methods

Described herein are non-surgical methods and devices for remodeling the tissues of the female genitalia by applying heat to a target tissue underlying the surface mucosal epithelium, while cooling the surface epithelium itself. Typically, the tissues are those of women who have had one or more vaginal births, and whose tissues have been stretched by giving birth. In particular, the target tissues (FIG. 8) are the connective tissue layers such as the lamina propria or submocosa 102 and the muscularis 104 underlying the mucosal epithelium 100 of genital tissues. Particular features or areas of genital tissue (FIG. 7) having an epithelial surface include the vulva and the vagina 112, and the introitus 114, the entrance to the vagina and a demarcation between the internal and external genitalia.

The heating of target tissue, per embodiments of this invention includes raising the temperature of the target tissue to as high as 80° C. Temperature is raised to a level that is therapeutic, i.e., to a temperature that causes remodeling, as described herein. That portion of the target tissue which attains the therapeutic temperature, for a sufficient time, is termed the therapeutic zone within the target tissue. The therapeutic temperature, in some cases may be only as high as 45° C., or as high as 80° C. Some variations of the therapeutic methods include heating target tissue to as high as 80° C. Target tissue may be heated to a temperature between about 45° C. and about 80° C. In other embodiments, the target tissue temperature may be heated to a temperature between about 50° C. and about 75° C. In still other embodiments, the target tissue may be heated to a temperature between about 55° C. and about 70° C.

The vagina is a fibromuscular tube, lined with stratified squamous epithelium that connects the external and internal organs of the female reproductive system. The vagina runs obliquely upwards and backwards at an angle of about 45 degrees between the bladder in front and the rectum and anus behind. In an adult female the anterior wall is about 7.5 cm long and the posterior wall is about 9 cm long. The difference in length is due to the angle of insertion of the cervix through the anterior wall. More particularly with regard to the vagina, embodiments of the invention comprise remodeling the lower portion of the vagina, the lower portion representing, the lower being that portion immediately inward from the introitus. Thus, according to embodiments of the invention, the portion of the vagina to be treated is a region between the introitus and a position located no further than about 3 to about 4 cm inward from the introitus. With regard to the circumferential aspects of the vagina, locations along the circumference of the vaginal wall may be assigned a clock position (see reference clock dial 136, in FIG. 7) such that the circumferential point closest to the urethra is at 12 o'clock. Using this orientation, embodiments of the invention comprise treating and remodeling the vagina over the 300 degree circumferential arc from about 1 o'clock to about 11 o'clock.

Figure 7:
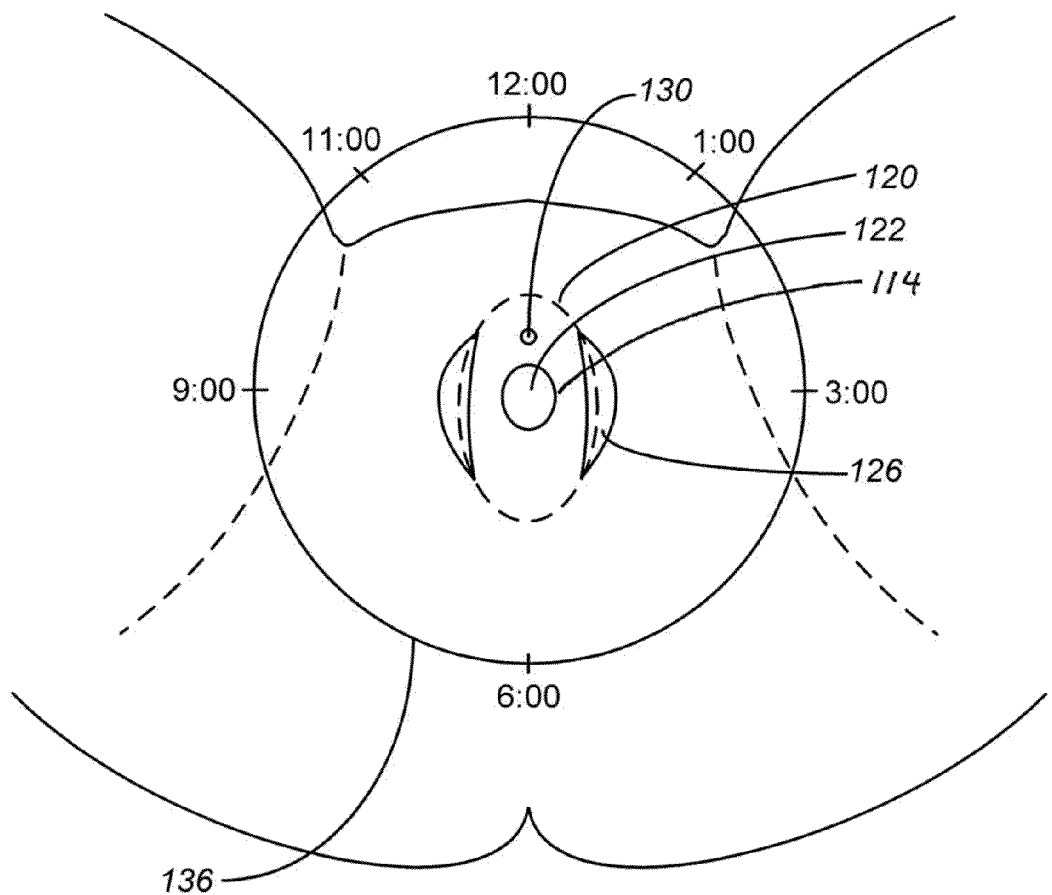
FIG. 7 is a schematic view of female genitalia depicting the mucosal epithelial surfaces that overlay the target tissue, as well as an orienting clock to provide a circumferential reference scheme for the vagina wall.

The mucosal epithelium of vulvar tissue outside the vagina and the introitus includes the labia minora, or that portion of the vulva extending outward from the introitus to Hart's line, the boundary where mucosal epithelium and labial skin meet (FIG. 7). The mucosal epithelium and the skin, while contiguous, are embryologically and histologically distinct. The portion of the female genitalia that are covered by epithelium is also substantially defined by the bounds of the vestibule, which extends outward or down from the hymenal ring at the top of the vagina, radially beyond the introitus, including the portion of labia minora located within Hart's line 120. The target tissue of embodiments of this invention include the connective tissue underlying these mucosal epithelial surfaces of the genitalia which, progressing down from the epithelial surface, are known as the lamina propria 102 and the muscularis 104 (FIG. 8), respectively (see, for example, Netter, Atlas of Human Anatomy, 4th edition, Saunders, 2006). The lamina propria includes a mixture of cells types that populate connective tissue, such as fibroblasts, and the muscularis is a layer of smooth muscle. Collagen is secreted or deposited into the extracellular space in these tissues by cells such as fibroblasts. These described target tissue layers below the epithelium overlay deeper tissues, including endopelvic fascia, are not typically targeted, and may not be affected by the systems described herein.

The remodeling of the connective tissue underlying the mucosal epithelial surfaces does not substantially affect the epithelium itself. The method and apparatus, as provided by embodiments of the invention are non-invasive and substantially non-ablative of genital issue. The nature of the engagement between the apparatus and genital tissue is that of contacting a treatment tip to an epithelial surface of the genital tissue. Through such contact, the apparatus delivers heat to underlying tissue, while preventing the heating of the surface epithelium by cooling it.

In a particular embodiment, the invention provides a method and apparatus for remodeling vulvar and vaginal target tissue through the use of a radiofrequency (RF) energy source 30 (see the energy delivery element of FIGS. 1-5) through the vaginal or vulvar mucosal epithelial tissue and to the respective underlying layers that are the target tissue of embodiments of the invention. Other embodiments may make use of other forms of energy, such as microwave or ultrasound. Impedance through mucosal epithelium is lower than that of skin, thus less energy is required to cause heating than would be required were skin being treated rather than mucosal epithelium.

The application of energy to the underlying connective tissue creates heat in the targeted tissue, and the heat is understood to have an immediate or nearly immediate effect of denaturing or partially-denaturing collagen in the tissue, this denaturation of collagen being a factor in the tissue remodeling. In other embodiments of the invention, the application of heat to the connective tissue during a treatment procedure is understood to result in a subsequent depositing of new or nascent collagen by cells of the connective tissue, as part of a biological process that may take place over the course of weeks or months following the procedure.

As provided by embodiments of the invention, remodeling of genital tissue, whether by denaturation of collagen in the tissue, or by subsequent deposition of new collagen in the tissue, results in a tightening of genital tissue, particularly that of the vagina and the introitus. A consequence of the heating of the target tissue may include a melting or denaturing of preexisting collagen in the tissue, which may reduce or compact the volume occupied by the collagen, the effect of which is to tighten surrounding tissue A longer term biological consequence of the heating may include a healing process in which there is an increase in the rate of cellular production and deposition into the extracellular space. Both types of responses, the near-immediate response of pre-existing collagen, and the longer term increased amount of collagen are understood to contribute to an overall tightening of the target tissue.

The tightening of tissue is such that the remodeled genitalia assumes a rejuvenated form, a conformation of the genitalia as they were before having being stretched by vaginal birth. Remodeling of genital tissue, as practiced by embodiments of this invention, may be understood variously as contracting or tightening of tissue, this may apply to the vulva, the vagina, and the introitus. Genitalia rejuvenated by practice of embodiments of the invention, by virtue of the greater tightness of the remodeled vagina and introitus, for example, provide for increased pressure and friction during sexual intercourse, and accordingly may provide greater sexual satisfaction for a woman with such remodeled genitalia and for her sexual partner.

Embodiments of the invention provide a method and apparatus for creating a reverse thermal gradient that utilizes one or more RF electrodes 30, to convey energy that manifests as heat in the target tissue, and a mechanism to cool the epithelial surface above the targeted underlying layers. A purpose of cooling the epithelial surface is to protect it from potentially damaging effects of excess heat that would accumulate in the absence of cooling. The epithelial surface is thus a conduit for energy passing through to underlying layers, but the energy does not manifest in the form of increased temperature at the epithelial surface. As such, the epithelium itself is not damaged or substantially modified by the method. Such protection from heating may derive both from the heat-sink aspect of a cooled body, as well as an increase in tissue impedance that is associated with cooled tissue.

In some embodiments, the cooling mechanism of the apparatus includes a lumen 54 adapted to accommodate a cooling fluid conveyed to nozzles 56, which cool the energy delivery element 30 of treatment tip 10 of the apparatus. Embodiments of the method thus provide for contacting a contact site on a genital epithelial surface, the tip having the capability both to cool the surface epithelium and to heat the underlying tissue. The cooling fluid cools the treatment tip of the apparatus, as provided by embodiments of the invention; in turn, the surface of the cooled treatment tip cools the surface of the mucosal epithelium that the treatment tip contacts. As provided by embodiments of the invention, the epithelial surface may be cooled to a temperature range of about 0° C. to about 10° C. As energy from the tip passes through the mucosal epithelial surface, the underlying soft tissue may be heated to a temperature range of about 45° C. to about 80° C. Thus, a reverse thermal gradient is created, with a lower temperature at the mucosal epithelium, and a higher temperature in the underlying tissue.

In some embodiments the method includes feedback control mechanisms to control the heating such that temperature does not exceed a predetermined level. As provided by embodiments of the apparatus, the feedback is provided to RF delivery by thermal or impedance sensors. In other embodiments, the method may be controlled by delivering a predetermined total of amount of energy. In some embodiments the method may be controlled by delivering an amount of energy within a predetermined amount of time.

More specifically within the target tissue of the invention, a treatment zone may be defined, where the heat is particularly focused, or where the heat reaches a threshold temperature sufficient to cause remodeling. Such a treatment zone may be centered at a particular depth below the epithelium, and the treatment zone may have a particular range of depth, it may, for example be broadly distributed across the full range of the lamina propria and muscularis, or it may occupy a relatively flat zone. In some embodiments of the invention, cooling is allowed to proceed into the target tissue itself, below the epithelial surface, to form a cold-protected tissue zone. The cooling of a portion of the target tissue may have an effect on the therapeutic zone, such that the depth and range of the therapeutic zone may be modulated or shifted with respect to where it would be absent such cooling of a portion of the target tissue. If cooling penetrates to a given level in the target tissue to create a cold-protected zone, for example, the therapeutic zone may be pushed deeper into the target tissue. Further, lower temperature in general tends to contain the dissemination of heat, thus focusing the therapeutic zone into a narrower range of depth.

In typical embodiments of the invention, the method provides for surface cooling coincident with the time that heat is being delivered to underlying tissue. In some embodiments, in addition to cooling the surface while heating the underlying tissue, the method includes a period of cooling before the application of heat. In other embodiments, the method includes a period of cooling after the application of heat. In still other embodiments, the method includes cooling both before and after the application of heat.

Figure 8:
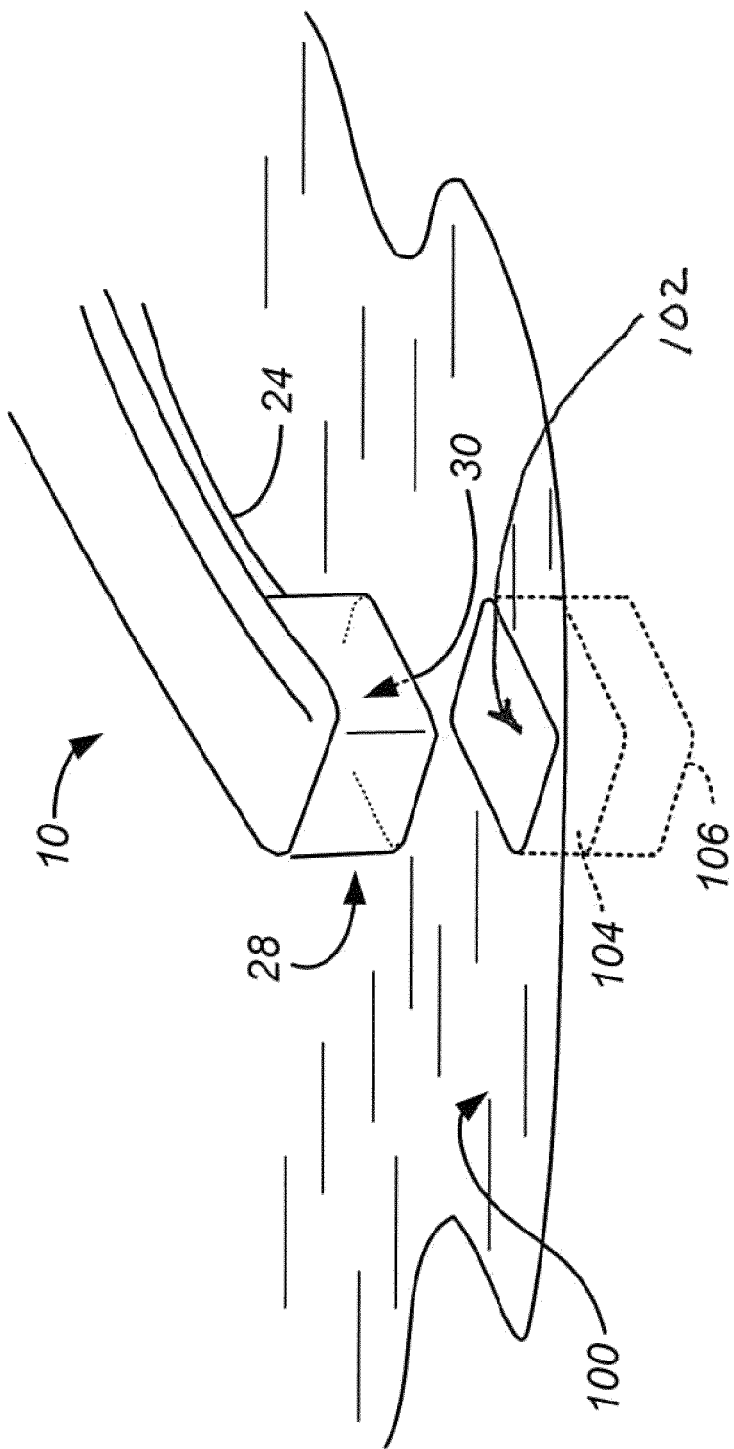
FIG. 8 shows a treatment tip contacting a genital epithelial mucosal surface and the underlying target tissue including the lamina propria and the muscularis.

As shown in FIG. 8, a treatment tip 10 of the apparatus contacts a contact site 102 on the genital epithelium 100, and such contact creating a site on the epithelium corresponding to the surface area within the outline of the profile of the treatment tip. FIG. 8 shows the distal end 28 of the tip, with the energy delivery element 30 (shown by dotted lines) facing toward the mucosal epithelium. Also shown below the contact site 102 (with dotted lines) are target tissue layers, the lamina propria 104 and the muscularis 106. In typical embodiments of the invention, the method includes making contact with the epithelium, delivering energy, and then moving the treatment tip to another contact site, and delivering energy there. A procedure, such as would take place in a visit to a medical office, would typically include a radial sequence of contacting the epithelium within the vagina and/or contacting other sites outside the vagina. During the same procedure, the treatment tip may be returned to the same contact point multiple times. The circumference of the lower portion of an unfolded vagina, gently stretched as it is during the practice of this method, is approximately 12 cm. Accordingly, with a treatment tip of about 1 cm in width, a series of about 10 contact sites allows completion of an 300 degree arc of the circumference, between the 1 o'clock and 11 o'clock positions. These dimensional considerations underlie the rationale for an embodiment of the treatment wherein the surface of the energy delivery element has a curvature of about 30 degrees, each contact site accounting for about 10% of the 300 degree arc.

Figure 9A:
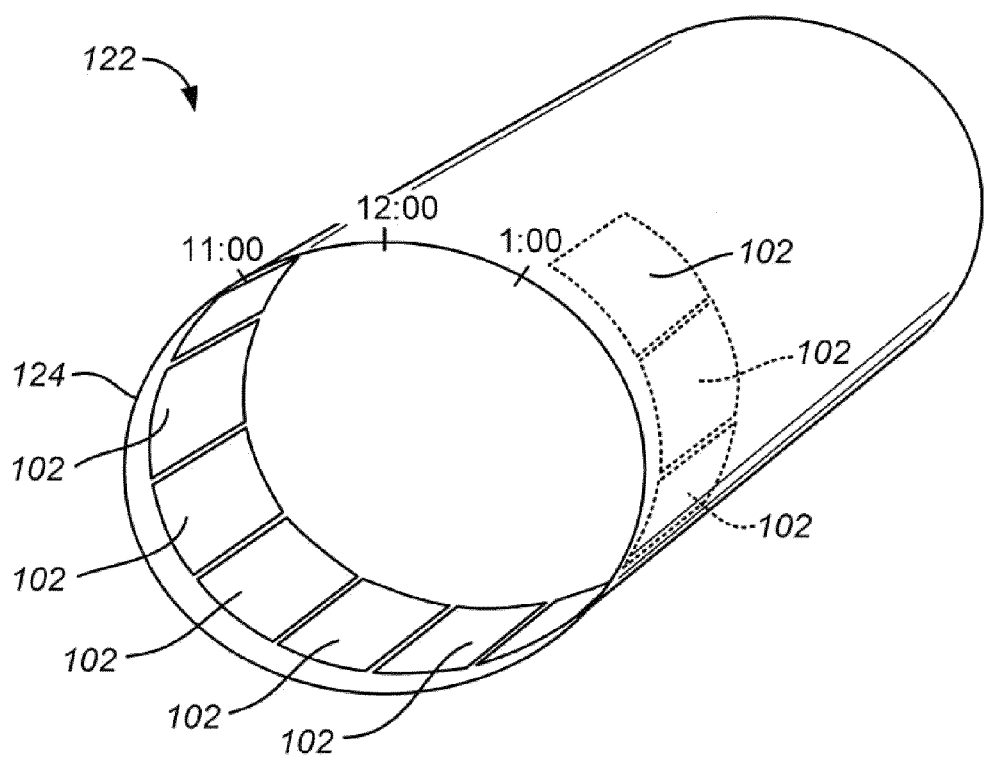
FIGS. 9A and 9B depict a treatment area of a mucosal epithelium comprising multiple contact sites (FIG. 9A), and a representation of the treatment area as a mapping grid (FIG. 9B).
Figure 9B:
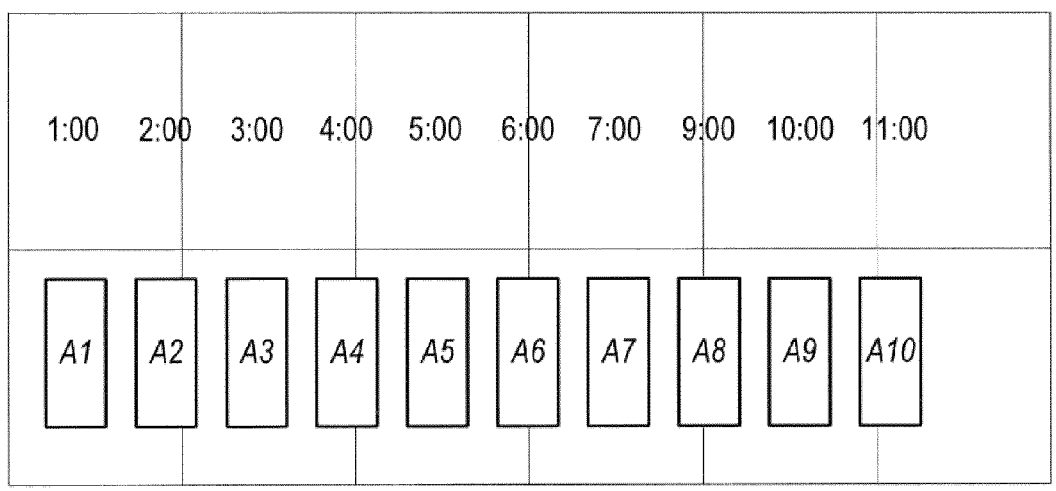

FIG. 9A is a schematic representation of a vagina 122, with the introitus 124 forming the entrance to the vagina. In a typical procedure, the treatment tip would contact various contact sites in the lower vagina, just inside the introitus. As shown in FIG. 9A, an accumulated set of contact sites 102 that have been treated by the treatment tip, and they collectively comprise a treatment area on the vaginal epithelium. In some embodiments of the method, a single radial row of sites is contacted, as shown in FIG. 9A. In other embodiments, one or more further rows could be included in a procedure, extending further into the vagina, so long as the treatment area remains in the lower portion of the vagina. Contact sites, per embodiments of the invention may include regions outside of the vagina, but within the bounds of Hart's line. Outside of the vagina, the treatment area will develop with a flatter aspect, in contrast to the inner radial configuration characteristic of the vaginal contact sites. As further provided by embodiments of the method and shown FIG. 9B, the contact sites may be recorded on a grid 115, the completed grid thus being a mapped representation of the treatment area, which can be referred to during evaluation of the remodeling at some time point following the treatment. As shown, the treatment grid may contain reference points with respect to the circumferential location on the vagina, as provided, for example, by the clock dial scheme.

As summarized above, a given treatment area may be treated during a single procedure during an office visit. The method further includes repetitions of such procedures, typically on another day, when the effects of the previous procedure may be evaluated. From such evaluation, judgment may be made with regard to re-treating a particular previously-treated area, or proceeding to treat other areas. Thus, as provided by embodiments of the method, one or more procedures during follow-up visits may variously include treating the same treatment area, treating an entirely different treatment area, or treating an overlapping treatment area, partially the same as previous area, and partially different.

As mentioned above, the cooling system typically includes an internal cooling of the applicator tip so that the energy delivery element is cooled during (and in some cases before and/or after) the application of energy to treat and remodel tissue. Any appropriate internal cooling system may be used, particularly those including the use of coolant such as a cryogen. In some variations the cooling may be electrical (e.g., via. Peltier effect or the like). Thus, the cooling system of the tip region may include a cooling chamber as illustrated above in FIGS. 2 and 3. The cooling chamber may include an open region into which one or more nozzles for spraying or applying coolant may be positioned across from a thermally conductive inner surface that is thermally continuous with the outer surface of the energy delivery element. The coolant may be applied to this inner surface to cool the energy delivery element. Coolant may be applied in any appropriate pattern to this inner surface. For example, FIG. 10A shows one variation of an inner surface 1001 of an energy delivery element that is thermally conductive.

Figure 10B:
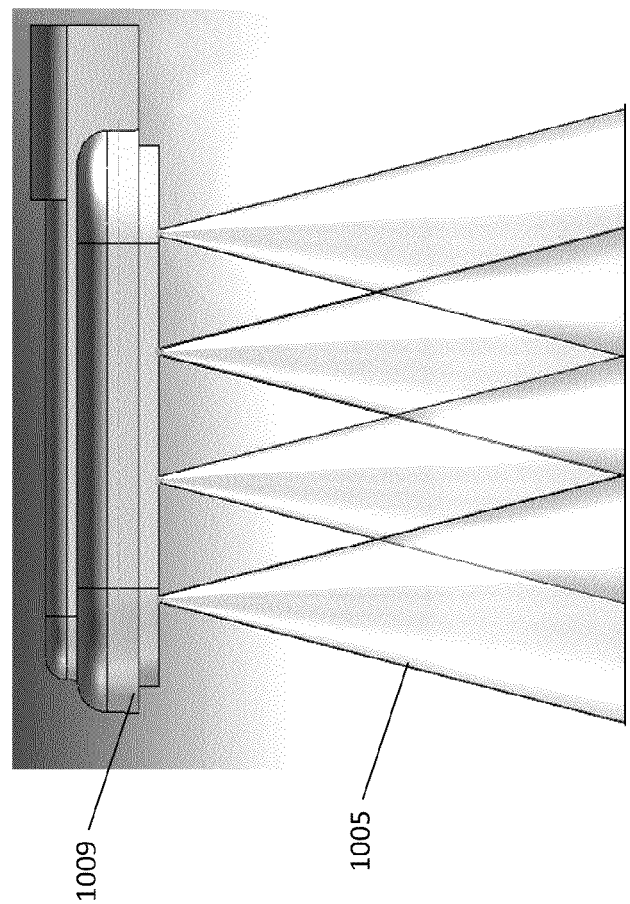
FIG. 10B illustrates a side perspective view of a coolant spray within an internal cooling cavity of the applicator tip shown in FIG. 4.
Figure 10A:
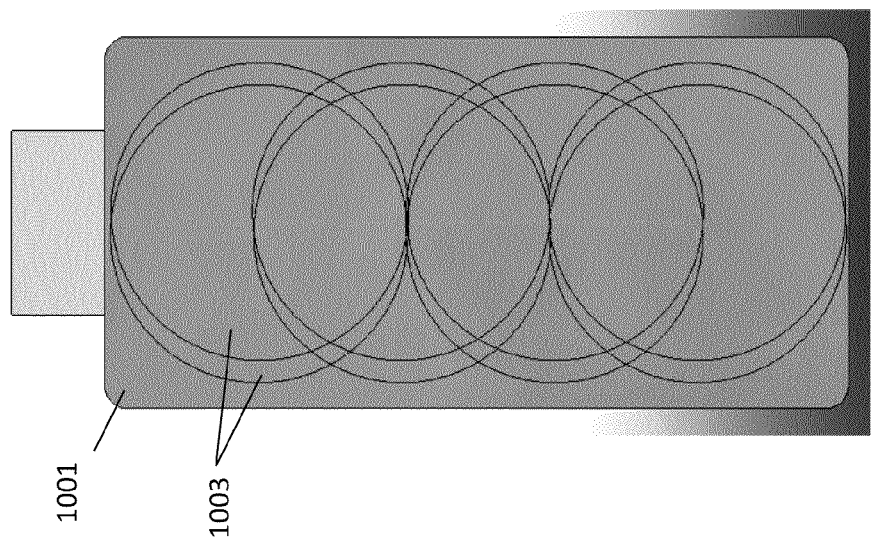
FIG. 10A shows a coolant spray pattern against an internal surface of an energy applicator such as the one shown in FIG. 4.

In FIG. 10A, the overlapping circles 1003 indicate the spray pattern of the coolant that is applied to the inner surface 1001 by eight nozzles, as shown in FIG. 10B. In FIG. 10B, the nozzles are spaced opposite of the inner surface 1001, and emit a cone-shaped spray pattern 1005 from the opposite surface 1009 of the cooling chamber.

Figure 11:
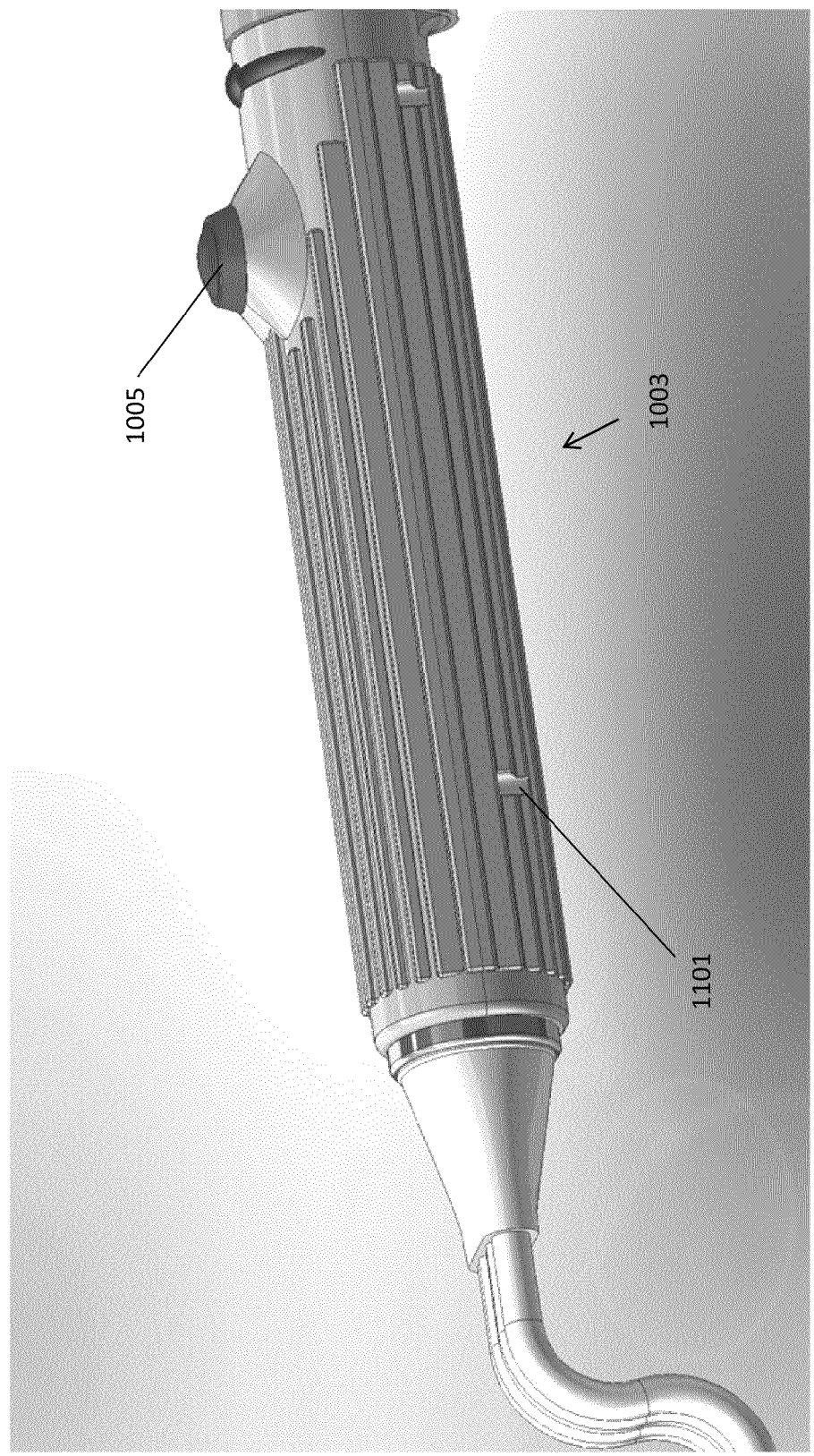
FIG. 11 illustrates one variation of a handle region of an applicator configured to connect to an applicator tip.

FIG. 11 illustrates another variation of a handle that may be used as part of an applicator device as described. In this variation, the handle 1101 is elongate, and includes a grip region 1003. The handle may also include one or more controls 1005 such as a button, slider, dial, or the like. The control may allow the user to apply energy to the energy delivery element, to apply coolant, or both. The handle may also include one or more indicators for indicating the status and/or orientation of the device, including the tip. For example, an indicator may indicate that the tip is attached/not attached. An indicator may indicate that the device is out of coolant. An indicator may indicate that the device is ready for activation. An indicator may indicate the temperature of the tip (e.g., the energy delivery element), and/or the time that the device has been active. Any appropriate indicator may be used. In some variations, the indicator includes one or more lights (e.g., LEDs, etc.), colors (including colored lights), alphanumeric (e.g., a display screen or monitor), or the like. The handle is typically configured to mate with the tip, as mentioned above. In some variations, the tip couples to the handle in a quick or easily attached and detached manner. Thus, the tip and/or handle may be configured for quick release and quick attachment.

Figure 13:
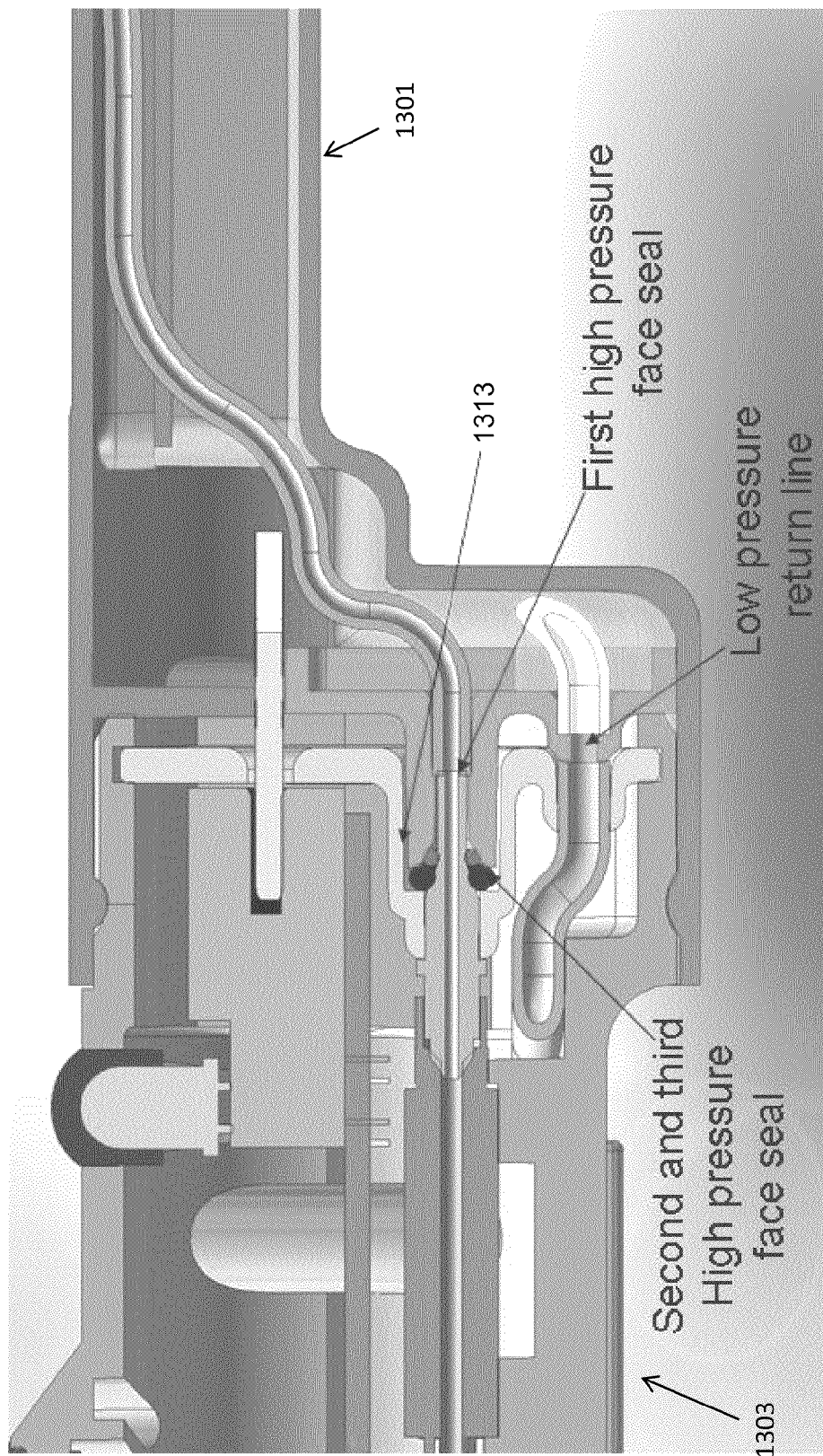
FIG. 13 shows a cross-section through the interface region of a tip and handle.

For example, FIG. 13 illustrates one variation of the attachment region between a tip 1301 and a handle 1303. The attachment region is adapted to make it easy and quick to attach/detach. The tip and handle are both configured to connect the electrical connector (powering the energy delivery element), and a coolant delivery line as well as coolant return line. The coolant delivery line is a channel through the handle and the tip through which coolant may be delivered for release within the cooling chamber, as described above. The coolant may be pressurized, and thus the connector must be adapted to handle the high pressures without leaking Thus, the device may include redundant seals at the interface between the tip and the handle, as shown in FIG. 13. For example, the high pressure seal may be configured as two or more (e.g., three) high pressure face seals. In this variation, the seals are not annular seals, which may reduce the pull-off force necessary to separate the tip and handle. In some variations, the coolant return line (or coolant return channel or pathway) is a low-pressure return line through which the coolant may be channeled. The coolant return line may be configured to remove coolant from the device (including the tip and handle region) so that it is not vented or released. In some variations the coolant return line does vent or release the coolant, but it releases it from a location that is remote to the patient and/or the technician operating the device. For example, the handle may include a coolant return channel that vents the coolant proximally, along a cord or connector from the handle, away from the patient.

The attachment handle 1301 may be easily attached and/or detached from the tip 1303. For example, regions of attachment 1313 may be configured to seal with a plurality of easy-release contact points, rather than a single sealing or contact point that would require more force to separate (such as annular seals). The seals may instead be configured to require only a small force to release. By increase the number of contacts/seals and/or the surface area of the seals, a lower release/connect force may be used to form a sufficiently stable connection. For example, the sealing surface area may be increased, which allows for a sufficient seal.

In some variations the coolant is collected and/or recycled. For example, the coolant return pathway may connect to a coolant return reservoir that collects used coolant. This coolant may be recycled or reused later. In some variations the system includes a compressor or recycler for reusing the coolant.

Figure 12:
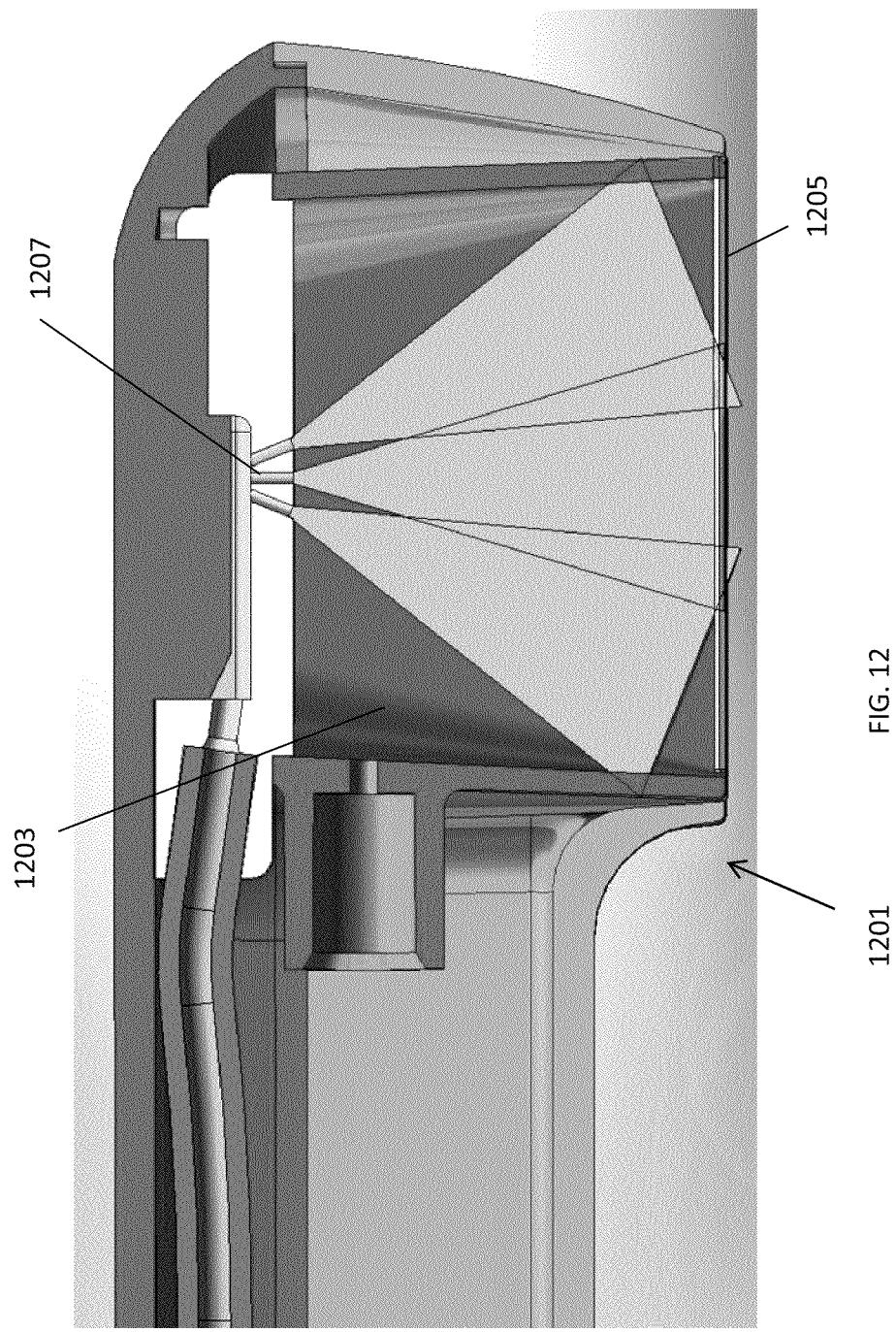
FIG. 12 is a longitudinal cross-section through a tip applicator of a device including the internal cooling chamber or lumen.

FIG. 12 shows a cross-section through another variation of a tip of a device 1201 including a cooling chamber 1203 having a plurality of (three) nozzles for applying coolant across the cooling chamber 1203 and onto an interior surface of the energy delivery component 1205. In this variation, the spray has been optimized so that the relatively large area of the internal surface of the energy delivery component 1205 will cooled by smaller cooling nozzles 1207. For example, in FIG. 12 the device includes three nozzles 1027 that are responsible for cooling the majority (virtually all) of the interior surface of the energy delivery component, as illustrated in FIG. 14A.

Figure 14B:
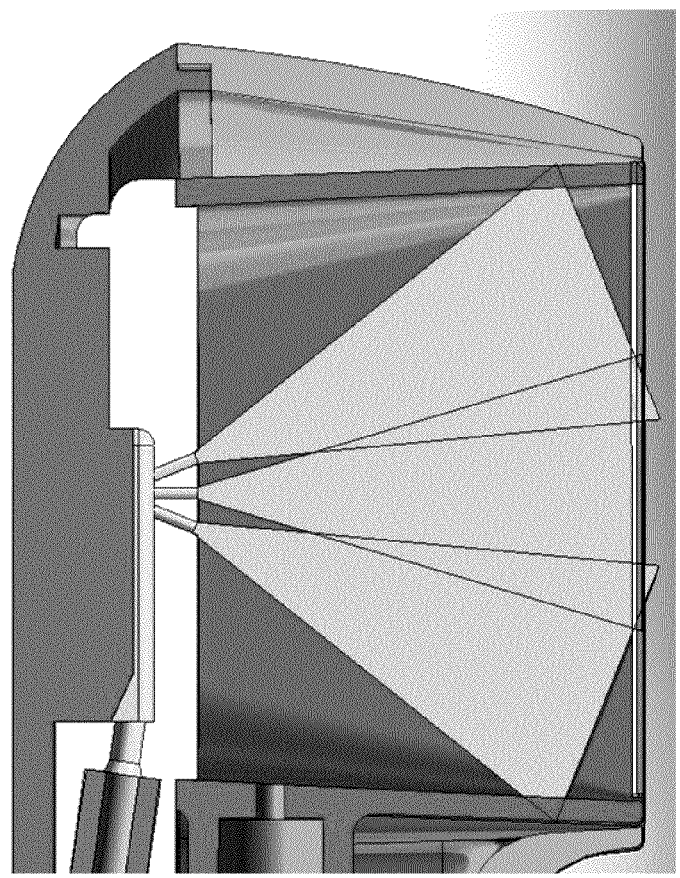
FIG. 14B illustrates a side perspective view of an applicator tip including a coolant spray being applied within an internal cooling cavity of the applicator tip.
Figure 14A:
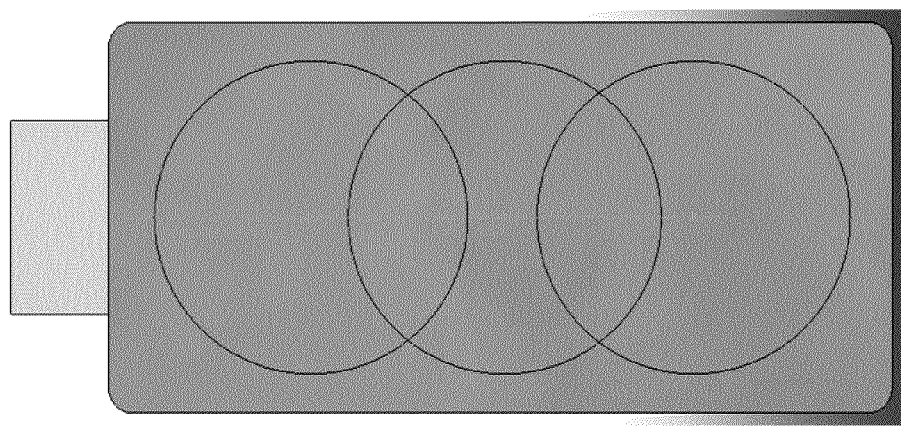
FIG. 14A shows a coolant spray pattern against an internal surface of an energy applicator.

FIGS. 14A and 14B show, respectively, the spray pattern of a device having only three nozzles for delivery of coolant within the housing. In this variation, the nozzles are angled to aim at longitudinally separated (though overlapping) regions of the interior surface of the energy delivery component, thereby cooling it. The arrangement illustrated in FIGS. 14A and 14B is believed to be more efficient than the configuration shown in FIGS. 10A and 10B, in which eight nozzles are used to apply coolant to the same space. Although there is less overlap of the coolant, it is believed that the energy delivery component can be cooled efficiently, in virtually the same time, as with a greater number of nozzles. The nozzles 1207 shown in FIGS. 14B and 12 (which illustrate the same variation) apply coolant to the majority of the thermally conductive inner surface of the energy delivery component. Since this inner surface is thermally conductive, cooling the inner surface (even a portion of the inner surface) will result in cooling the outer surface of the energy delivery component of the tip, and thereby cooling of the tissue in contact with this tip.

System

A vaginal remodeling system may include a handle, a disposable (or reusable) treatment tip, a power source/supply, a plurality of temperature sensors, a cooling sub-system, and a controller. In some variations, the controller, power supply/source and cooling sub-system may be integrated into a single unit to which the handle and tip may be coupled. This entire system may be configured for ease of use, including portability and compact arrangement.

For example, in one variation, the system may include: a treatment tip (for delivery of RF energy), a source of coolant (e.g., cryogen), a hand piece (handle), a cable connecting the handle and tip to the source of coolant and/or power source and/or control system, a power source (e.g., RF generator), and a controller. Optionally, the system may also include a coupling fluid, a return pad, a separate control switch (e.g., footswitch).

As mentioned, in some variations, the controller, power source (RF generator) and cooling system may all be integrated into a single unit that is connected (via one or more cables) to the hand piece and treatment tip. For example, FIGS. 15A-15F illustrate one variation of a system including the integrated controller with power source and coolant that connects to the hand piece and tip.

Figure 15A:
FIGS. 15A-15F illustrate one variation of a system for treating the vagina and adjacent tissues, including a handle (hand piece) and treatment tip connected to an integrated controller, power supply and coolant.

FIG. 15A shows a front view of the integrated system, in which the handle is connected via a single cable to a chassis containing the controller, cooling system and RF power source. For convenience, the integrated controller, cooling system and RF power source will be referred to as an integrated controller, which includes both the integrated cooling system and power source that may be controlled or regulated by the controller. The system 1500 in this example includes a display 1501 and a housing 1503 to which the hand piece (handle 1505) and treatment tip 1507 are attached via a cable 1509. The cable may include supply and return coolant lines, as well as a connection to the RF energy supply and any sensor(s) on the treatment tip.

Figure 15B:
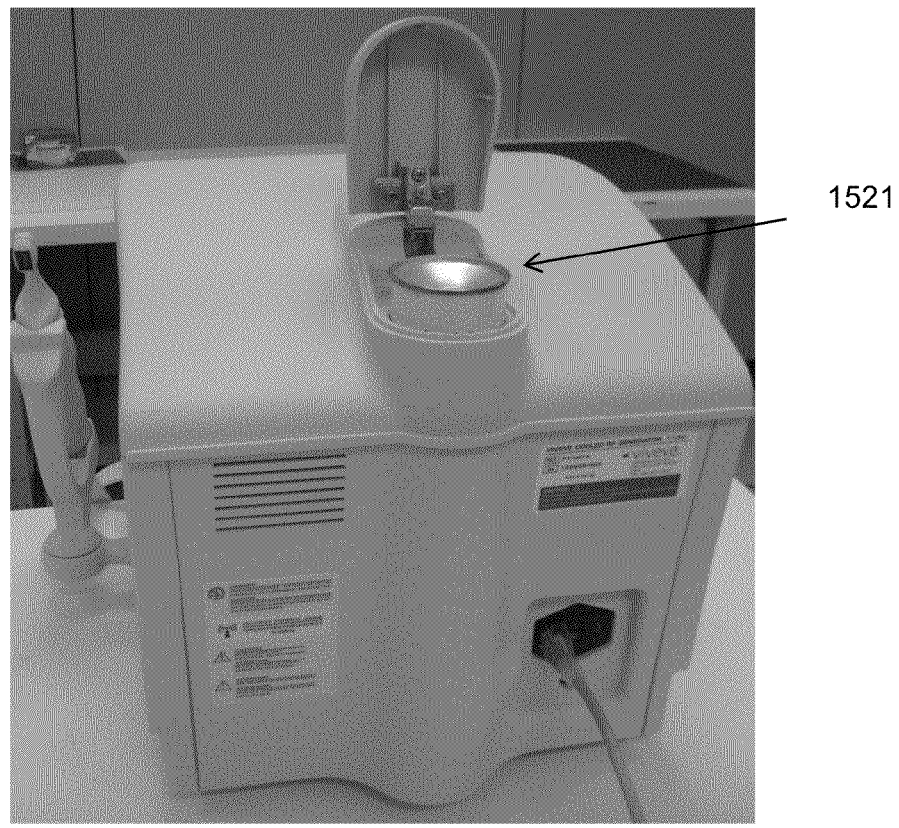
Figure 15C:
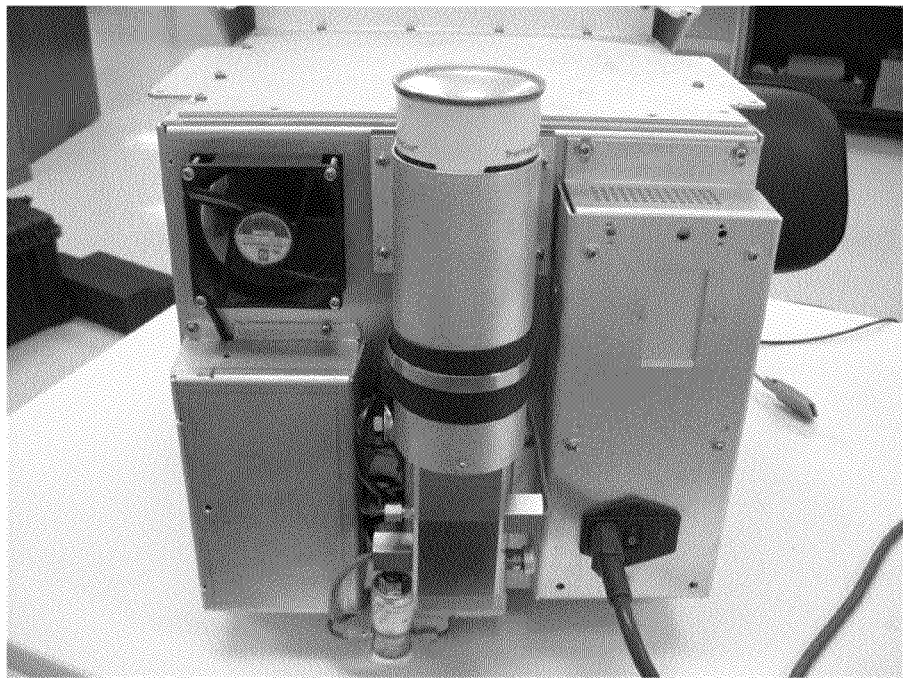
Figure 15D:
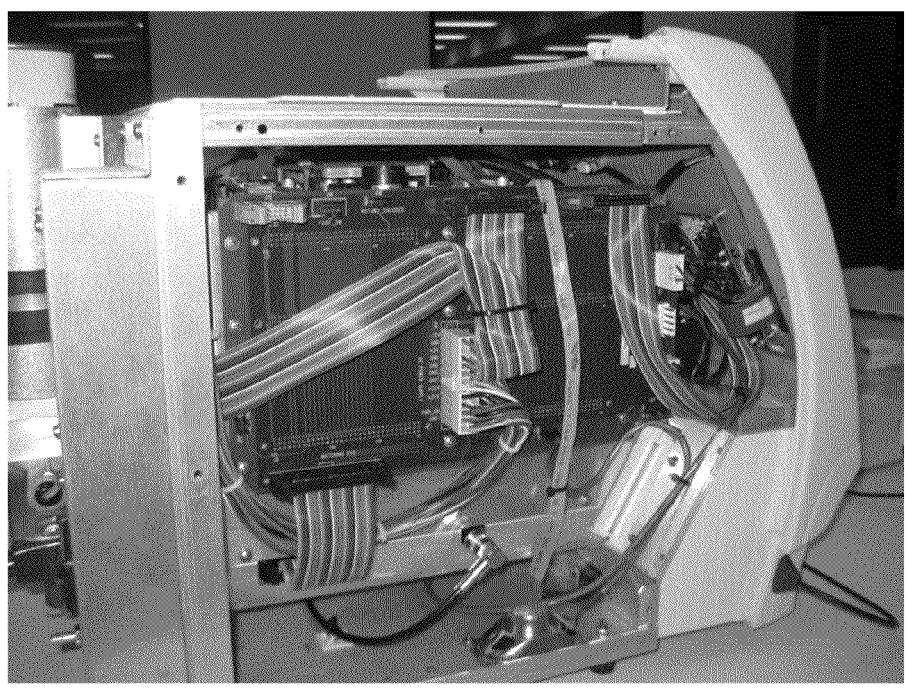
Figure 15E:
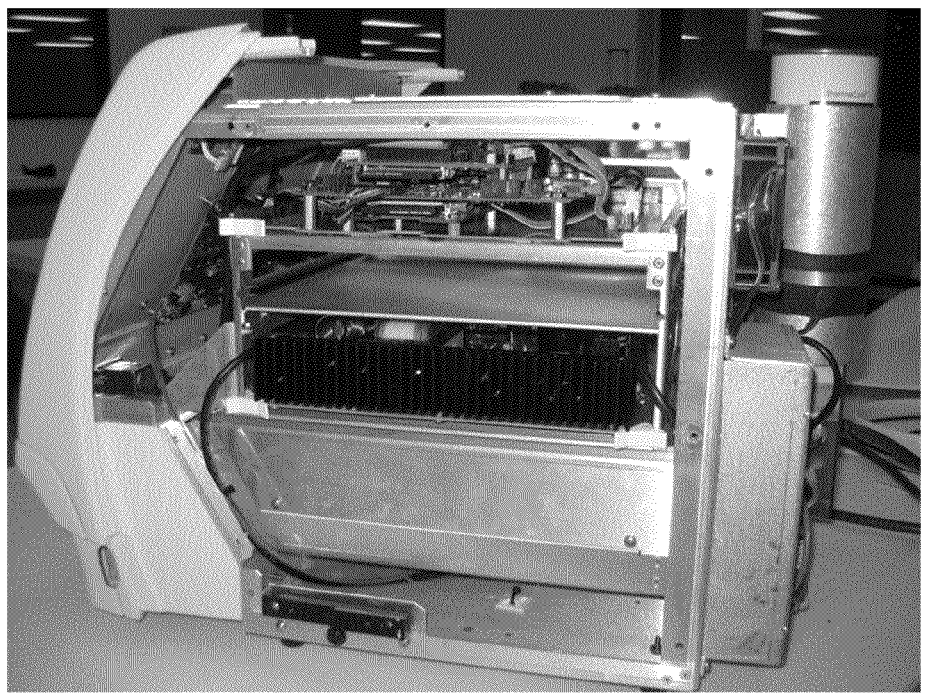
Figure 15F:
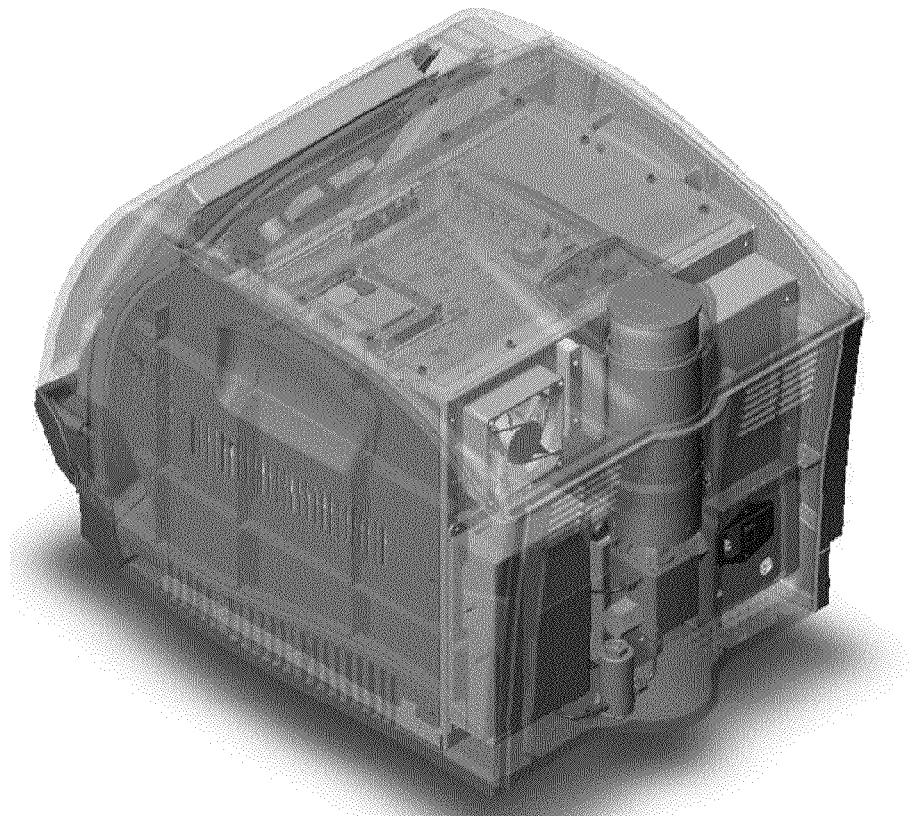

FIG. 15B illustrates the back of the device, including an opening into which a coolant may be inserted. In this example the coolant is a canister of coolant 1521 that may be attached into the opening and secured in place to provide coolant to the system. FIGS. 15C-15F show back and side perspective views of the system with the housing removed, exposing the chassis that supports the controller (microprocessor), cooling system and RF power source.

In this example, the integrated coolant includes a canister 1521 that can be secured into the opening in the housing. For example, the coolant may be a pressurized canister of cryogen such as R-134A or other appropriate coolant. In this example, the coolant canister may be threaded with one or more sets of threads to secure it into place in the integrated controller, although any appropriate sealing mechanism for the coolant may be used. The level of coolant may be monitored by the controller, and the display may include an icon indicating the level of coolant remaining in the canister or system (see, e.g., FIGS. 20A-20C, described in greater detail below).

Figure 19B:
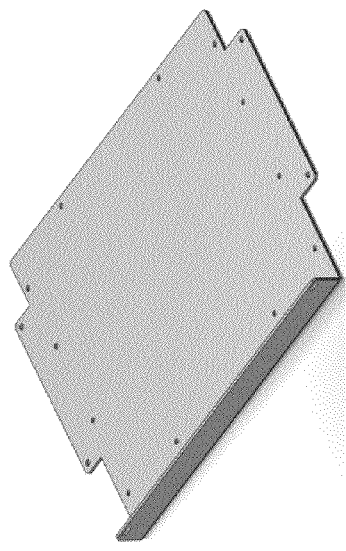
FIGS. 19A-19E illustrate one variation of the internal chassis forming the integrated controller, power generator and coolant system to which the handle is attached.
Figure 19D:
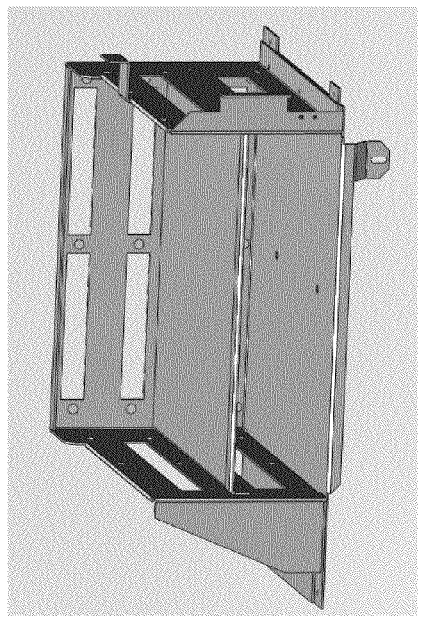
Figure 19A:
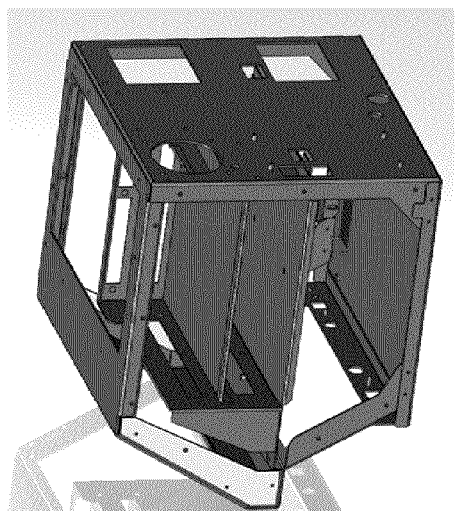
Figure 19C:
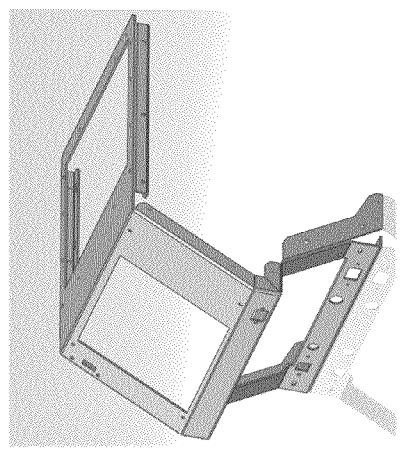
Figure 19E:
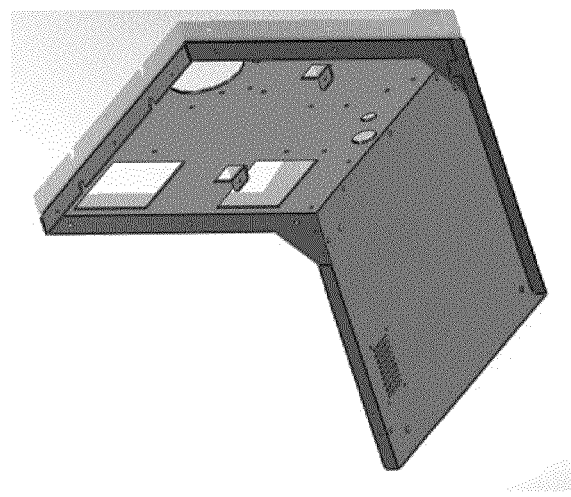

One example of the chassis of the integrated system is shown in FIGS. 19A-19E. The chassis supports the components of the integrated controller, such as a microprocessor (which may include hardware, software, and/or firmware) for controlling the system), any outputs (e.g., monitor, one or more speakers, etc.) the RF power source, and the cooling sub-system. These different portions of the integrated controller may be partitioned within the housing, in the support chassis, in a manner that allows them to be "modular." For example, all or portions of the integrated controller may be modular to allow them to be easily swapped out with new or refurbished components. For example, FIG. 19A shows a side view of a chassis with all of the components removed. Removing the side panels of the housing may exposing the internal regions or compartments into which the various components are positioned. FIG. 19B shows a perspective view of a top piece of the chassis, which may also be removable, while FIGS. 19C and 19D show perspective views of the front and internal regions of the chassis. FIG. 19E shows a perspective view of the back and bottom pieces of the chassis.

The chassis may include rails or mounts that allow various regions or components to be inserted and removed (pulled out) easily. The overall arrangement of components in the housing may include vertical and horizontal boards or regions, which may be readily accessible.

In the example, system shown in FIGS. 15A-15F, the handle and tip are shown attached to the side of the device, near the front. In some variations the handle is attached to the integrated controller from a central, front region. This may allow the maximum reach of the handle regardless of the orientation (or handedness) of the user of the device. The integrated controller may also include a holder or cradle for the hand piece. In some variations the controller housing may include a cradle housing built into the housing, or extending from either (or both) sides of the housing.

Figure 16A:
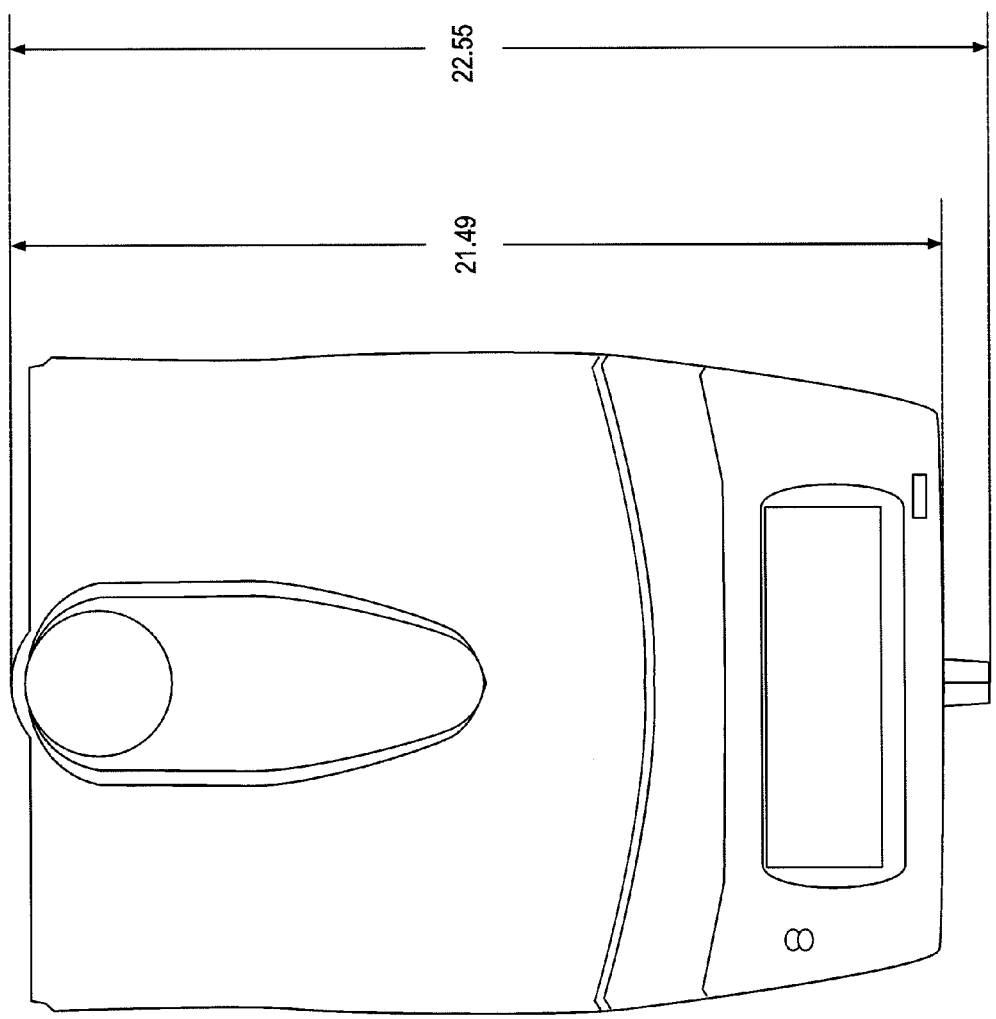
FIGS. 16A-16C show various views and exemplary dimensions of a system such as the one shown in FIGS. 15A-15F.
Figure 16C:
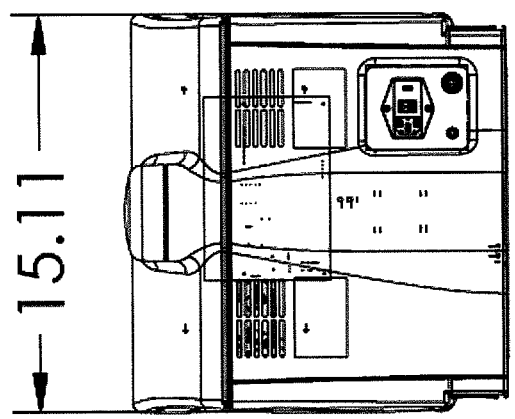
Figure 16B:
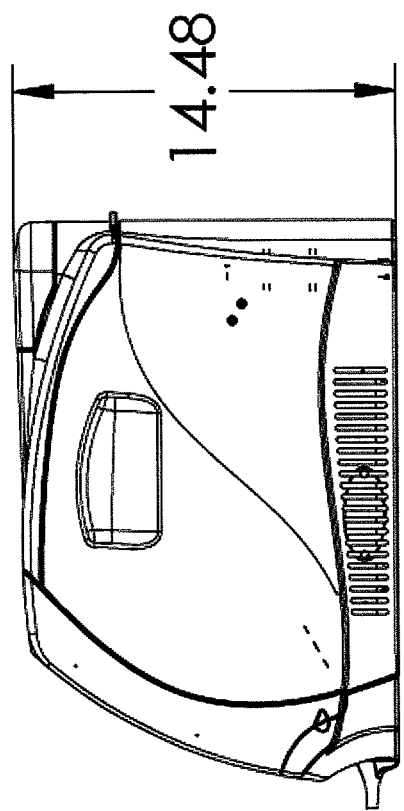

The overall weight and footprint of the system, and particularly the integrated controller, may be sufficiently small so that the device is portable and readily storable, which may be important for moving between surgical theaters or clinics. For example, FIGS. 16A-16C illustrate one exemplary set of dimensions for a system including an integrated controller (integrating the controller, RF generator and cooling system). In this example, the integrated controller is less than approximately 23 inches long (deep), 15 inches high, and 16 inches wide. The entire system may weigh less than 50 pounds.

The system may also include one or more controls for controlling the device. In particular, the system may include a control for delivering the energy from the treatment tip (e.g., activation control), as well as one or more controls for controlling the treatment regime, e.g., communicating with the integrated controller.

In the example shown in FIG. 15A, the display screen shown is a touch screen that allows the user to select treatment parameters by touching the screen. As mentioned above, in some variations, the system may include a keyboard, mouse, trackball, or the like.

In some variations, the activation control is included on the hand piece (e.g., handle), by including a button, as shown in the exemplary handles discussed above. However, it may be unexpectedly advantageous to include a treatment handle that does not include a button such as an activation control. As described above, since the user may be applying energy to the device to treat from a variety or orientations relative to the (typically prone) patient, it may be more convenient to include a foot switch for control of activation. Thus, in some variations the system may include a wired or wireless foot switch or other control that is separate from the hand piece. In one variation the foot switch is connected to the integrated control (e.g., by a cord or wire extending from the housing).

As mentioned, the hand piece (handle) is typically connected to the integrated controller by a cable or cord (including a delivery/return for coolant, power, etc.). The length of the hand piece cord may be optimized for flexibility, support strength and length. The cable must have sufficient support to allow delivery and return of the coolant (in addition to power lines for the RF energy and/or any sensors) without kinking, which may otherwise block or prevent delivery of the coolant to the treatment tip. However, cables having sufficient strength for use with the coolant may be overly thick or rigid, making handling difficult. It was determined that a flat cable (as illustrated herein) in which the various channels are arranged in parallel, may permit sufficient flexibility to allow ease of control without sacrificing strength. In contrast, a round cable may be more rigid and more difficult to control.

Similarly, in some variations, the system may include a rotatable connector for the cable, either at the hand piece or at the controller housing, or both. A rotatable connector may allow the hand piece to be rotated relative to the cord/cable (e.g., relative to the length of the cord). This may make the hand piece easier to use during treatment, where it may be rotated to treat different patient regions. In addition, the system may include modifications to increase user comfort when treating the patient, particularly given the necessary weight of the handle and cable. For example, in some variations the system includes a holder to hold the cable up, above the working area, so that the user does not have to support the full weight of the cord/cable. In some variations, the cord/cable is approximately six feet long, or shorter.

As described in greater detail below, the hand piece or handle may also be adapted to increase the comfort and ease of use. In addition to removing the switch, as mentioned above.

Handle

Figure 17A:
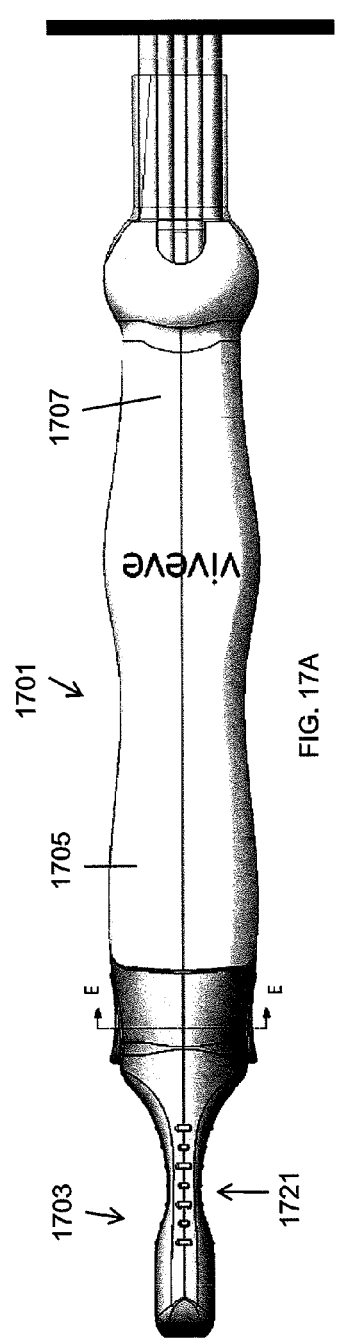
FIGS. 17A-17C illustrate one variation of a handle including a treatment tip, shown from a top, side and bottom views, respectively.
Figure 17C:
Figure 17B:
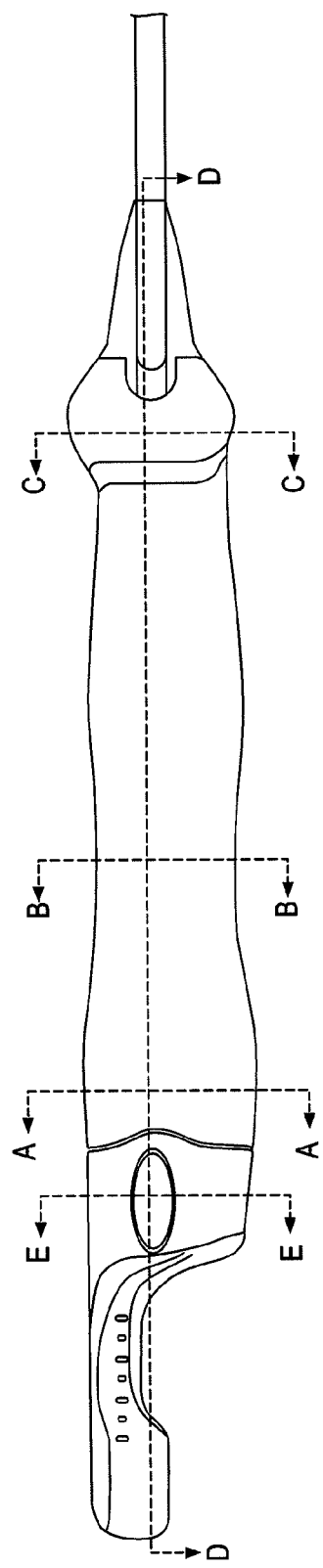

FIGS. 17A-17C illustrate one variation of a hand piece (handle) for a vaginal remodeling device. This variation includes adaptations enhancing the control of the hand piece during treatment of a typical patient. One difficulty in treating patients using any of the remodeling devices described herein or known in the art is the fatigue experienced by the operator in manipulating the handle. The typical handle may be awkward to use, particularly since the handle may need to be held against the patient's tissue sufficient to maintain the electrical connection with the tissue for the effective delivery of RF energy. In addition, the device must be held a proper orientation relative to the patient. The vagina surfaces are angled relative to the vaginal opening, requiring that the user rotate the handle relative to the patient from various angles in order to achieve complete coverage of the treatment area.

In FIGS. 17A-17C, the hand piece 1701 (shown with attached tip 1703) is an elongate handle configured so that it can readily be held by two hands, although it may be sufficiently light enough to be held by one hand. For example, the handle may be somewhat straight (elongate) extending proximally from the distal treatment tip along the same axis as the treatment tip. The handle may include two gripping regions, which may include two or more shallow "neck" regions forming the gripping regions 1705, 1707. As described above, the treatment tip may be connected and include sealing regions to seal the coolant delivery and return lines. The handle may be free of the actuating buttons (although in some variations it may include an activation button); and may be used with a foot switch or other activation switch.

In some variations either the hand piece or the treatment tip, or both, includes markings 1721 that may indicate depth within the vagina. This may allow the user to maintain a desired depth of use.

FIGS. 18A-18D illustrate various cross-sections through the exemplary handle shown in FIGS. 17A-17C.

Figure 18B:
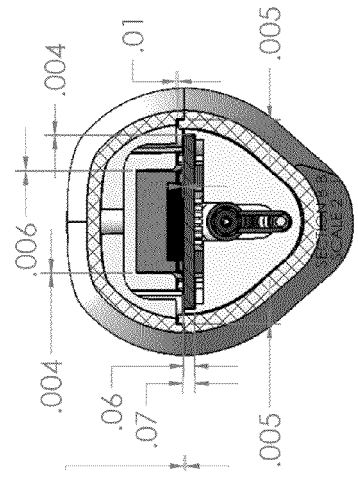
FIGS. 18A-18E show cross-sections through the exemplary handle shown in FIGS. 17A-17C.
Figure 18E:
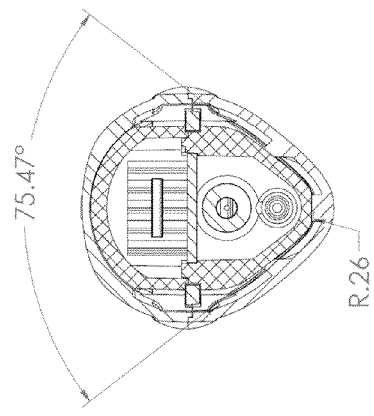
Figure 18A:
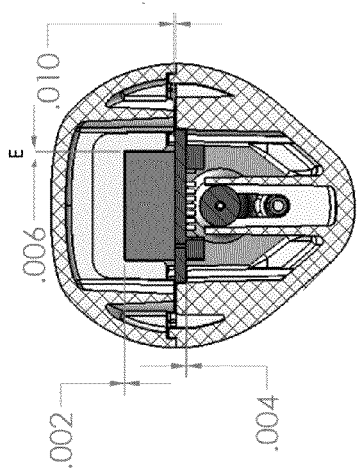
Figure 18C:
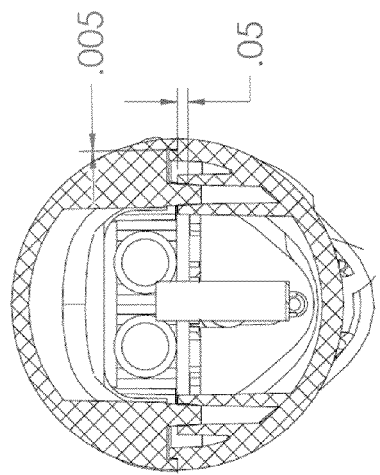
Figure 18D:
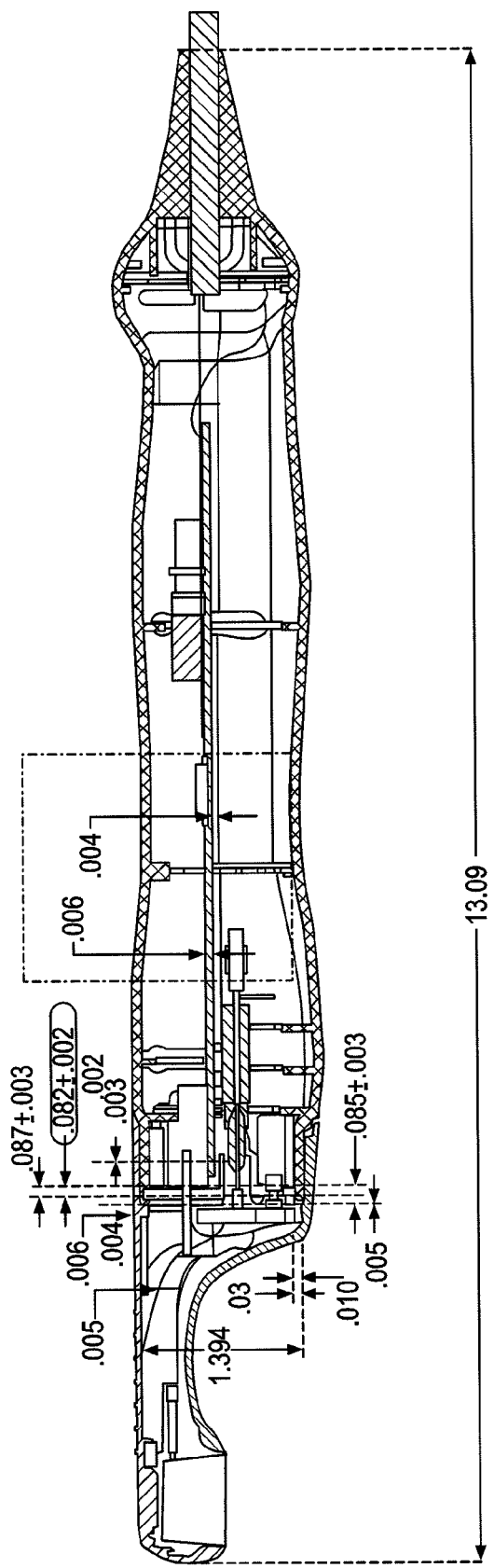

In the example shown in FIGS. 17A-18D, the hand piece and tip are approximately 13 inches long. The dimensions shown in FIGS. 18A-18D are exemplary only; these dimensions (shown in inches) may be modified without deviating from the invention. In general, the handle is sufficiently long to be easily held by two hands. The handle may be relatively rigid (compared to the flexible, typically flat cable, for example). In some variations, the handle is between about 8 inches and about 16 inches long (e.g., greater than 8 inches long, greater than 9 inches long, greater than 10 inches long, greater than 11 inches long, greater than 12 inches long, greater than 13 inches long, greater than 14 inches long, etc.). In some variations, the handle (including the treatment tip) is preferably greater than about 12 inches long (e.g., 13 inches long) because it may allow two-handed use. The handle may be rigid and lightweight (e.g., the inner region may be relatively hollow, as shown in FIG. 18D). Thus, the handle may be manipulated with a single hand, though long enough for two-handed use.

Control System

The controller, including the integrated controllers described above, may include a display that is configured to display information about the procedure, the coolant, the treatment tip, handle and other components of the system. This information may be displayed on the front of the integrated controller, and may present the information with audio signals as well. The display may also be used to display error information (including error codes) based on the status of the various system component (e.g., coolant level, contact with skin, RF generator status, etc.).

Figure 20A:
FIGS. 20A-20C show different examples of control screens for an exemplary system as described herein.
Figure 20B:
Figure 20C:

In one particular example, the system includes a display indicating the status of the treatment tip. The treatment tip may include a plurality of RF electrodes. For example, the tip may include an array of four electrodes arranged adjacent to each other. The tip may also include a plurality of sensor for indicating if each electrode is in appropriate contact with the tissue to be treated. FIGS. 20A-20C illustrate three exemplary "screens" of the display.

In FIG. 20A the screen has been divided up into five regions displaying status information and instructions to the user. For example, the upper right portion of the screen indicates the coolant level 2001 in a meter icon (slider). Below that is a graphical representation of the electrodes on the treatment tip 2003. In this example, there are four quadrants (1-4). These labeled quadrants may include a visual indicator that indicates if the electrode sufficiently contacting the patient for effective treatment. As mentioned above, in some variations this indicator may reflect an impedance and/or thermal measurement. In some variations it is desirable to use a non-electrical (e.g., non-resistance or electrical impedance) determination of contact with the patient; and example of a method and system for achieving this is described below. In FIG. 20A the contact map 2003 indicates that each of the four quadrants is in sufficient contact. In this case the bottom region 2005 of the display informs the user that the treatment may be started by pushing the foot switch. FIGS. 20B and 20C are similar to FIG. 20A except that the contact maps indicate that the electrodes of the treatment tip are not in sufficient contact with the patient. In FIG. 20B none of the electrodes are determined to be in sufficient contact, and therefore the system instructs the user to "make patient contact" before treatment can proceed. In FIG. 20C, the contact map indicates that half (2 of 4) of the electrodes are in sufficient contact with the patient, and the information icon instructs the user to "make better contact." FIGS. 20A-20C all indicate the treatment level to be applied (90 Joules/cm$^2$ in this example), as well as the remaining tip pulses to be applied (100 in this example). A slider below the remaining tip pulses indicator visually indicates the number of pulses to be delivered for treatment. In some variations these parameters (the treatment level and the pulses applied to treat) may be selected or modified by pressing the "settings" button 2009 and altering or inputting the values.

In operation, the user may use a touch screen to begin using the device, including selecting stimulation parameters such as the treatment level and pulses to be delivered. Below is one description of a proposed method of using the devices described herein.

A. Set Up: Tuning the Treatment Tip

Prior to treatment, in some variations the system may be "tuned."

The system typically includes a handle and treatment tip that is configured to seal and removably connect to the handle, an integrated controller, RF generator and cooling sub-system, a cable or cord connecting the handle and tip to the controller, and an activation foot switch to connect to the controller. The system may also include a return pad (electrical return), a canister of cryogen (coolant), and a coupling fluid. The coupling fluid may be provided to help make sufficient electrical contact between the tip and the patient's tissue.

In some variations, the system may be self-tuning. In some variations, the system may allow the user to tune the applicator. To tune the system, the tip, handle and controller may be matched. Upon installing a treatment tip onto the generator's hand piece, the generator's user interface screen may be configured to require a tuning cycle in order to set the desired RF energy level. The following steps should be executed to complete the tuning cycle:

First, confirm that the generator system's cables are properly connected and that the patient return electrode pad is fully and properly placed onto the patient.

Next, after installing the treatment tip onto the hand piece, wait unit the generator's user interface screen reads ready for tuning. Push the confirm button on the generator's front panel and then push the start/stop button. The generator's start/stop button should now be flashing. If not flashing, press confirm and the start/stop button again. If the start/stop button does not begin to flash, uninstall and reinstall treatment tip onto the hand piece and repeat, pushing the confirm button and the start/stop button.

Thereafter, apply coupling fluid to the treatment tip's electrode surface and then place the electrode onto the target tissue inside the vaginal introits. Make sure the entire electrode surface is evenly seated onto the vaginal tissue. The blue light on the hand piece will illuminate when the appropriate tissue temperature is reached.

With the blue light on the hand piece illuminated and while maintaining tissue contact with the electrode surface, press the RF activation button located on the hand piece or footswitch and hold down until the generator's user interface screen displays tuning complete. Occasionally, the generator may require more than one tuning cycle to complete the tuning process. If so, repeat placing the electrode onto the target tissue and push and hold down the RF activation button until tuning is complete.

In some variations the system does not need to be tuned, but may be pre-turned or matched.

In some variations, the system may allow the RF energy level to be set to a desired level, prior to starting the procedure. For example, using a control (e.g., a knob on the front panel, a graphical interface control using the touch screen, etc.), the RF energy level may be changed, e.g., to 18.0 (180 J) and then confirm and the start/stop buttons or other controls may be pushed.

In some variations of the system, the energy level of the controller is not adjustable, but is fixed at a particular energy level or range of energy levels that have been found to be effective. For example, in some variations of the system, the energy level of the controller is fixed at approximately 90 J. In other variations, the energy level is constrained to be within a range of about 80 J to about 130 J (e.g., 90 J to 120 J).

Procedural Set Up

In some variations, the treatment area may be defined as the mucosal surface of the vaginal introitus starting at the hymenal ring, for example, the region covering the area from the 1:00 to 11:00 position and avoiding the areas immediately below and adjacent to the urethra. To set-up for treatment, the user may first clean and prepare the treatment area and the surrounding surface of the vagina with a non-alcohol based cleaner. The user may then confirm that the integrated control (RF Generator, cooling module and control), hand piece and foot switch (if used), are set up properly, and properly connected.

Thereafter, the patient return pad electrode may be placed in contact with a clean dry area of the skin on the lower back or side area (above the hip) of the patient and the treatment tip may be fully pressed onto the hand piece before using. Optimally, the treatment tip should be in full contact with mucosal tissue for safe operation. To treat, the treatment area and treatment tip may be bathed with coupling fluid to ensure good electrical contact with the treatment surface. Additional coupling fluid may be applied during the treatment procedure.

The user may use the device with a retractor, if desired, although care should be taken not to contact the applicator (electrodes) of the treatment tip to any retractors. In some variations, the energy setting is 180 J. The energy density is 90 J/cm$^2$. While ensuring the treatment tip is in good contact with the treatment surface and confirming that the blue light on the hand piece is illuminated, the RF energy may be applied to the target area by activating the switch on the hand piece or footswitch.

In some variations (e.g., using the treatment tips and devices described herein), each energy application may treat a 1 cm×2 cm area. Starting clockwise, the treatment tip may be applied to the vaginal mucosal surface of the vaginal introitus staring at the hymenal ring, covering the entire area from 1:00 to 11:00 o'clock position, avoiding the urethra. To ensure complete coverage, the energy application may overlap by 50% or 0.5 cm$^2$. This step may be repeated until a total of five (5) passes are made in the treatment area.

Confirmation of Contact and System Control

As mentioned above, the system may be configured to confirm that the applicator tip and particularly the energy applicators (e.g., electrodes) are in good contact with the tissue to assure that the tissue will be treated adequately, and to prevent injury. In some variations the system includes a display that includes a "contact map" that shows (by color, symbol, text, etc.) that the appropriate contact are being made with the tip and/or the energy applicators. For example, the contact map may display a map of the energy applicators indicating sufficient patient contact for each energy applicator region. In FIGS. 20A-20C, for example, the system shows a four-quadrant map of the applicator tip and indicates if the energy applicator is in sufficient contact with the patient.

In some variations, adequate contact means adequate electrical contact, and may be determined by applying a low level of electrical current from the electrodes to determine if the contact is sufficient (e.g., measuring the resistance/conductance between the electrodes and the tissue). This has unexpected led to problems, however, as EMC (electrical interference) testing of the devices including an RF generator have demonstrated unacceptable amounts of generated interference on the power line connections. This problem may lead to the system (e.g., the generator) failing to comply with EMC limits.

The reason for this problem may be inherent in the use of electrical testing of the contact. For example, RF generator tissue contact algorithms typically use electrical impedance measurements to detect whether the tip is completely in air or in partial contact with the tissue prior to delivering therapeutic RF energy. Impedance measurements require that the RF output circuitry be energized at a low level. This low level produces electrical interference on the power line connections. Although RF generators are usually exempted from complying with EMC limits during therapeutic energy delivery, this exemption may not apply to pre-application (e.g., contact testing).

A system and method of determining tip-to-tissue contact that does not require the energizing of the RF output circuitry prior to delivering therapeutic energy is described herein.

In some variations the systems described herein, the treatment tips include a plurality of temperature sensing elements (e.g., thermisters). For example, the system may include six thermisters, surrounding (e.g., at the edges of) the four electrodes. In one variation the system may use a combination of the temperature information from all or a sub-set of the thermisters and the usage history and timing of the device to determine if there is sufficient contact with the patient for operation of the system.

In one variation, which may be used with an impedance/resistance measurement, if the system determines that an electrode has a high impedance that is typically of the impedance in air, the system will indicate that the electrode is not in contact with the tissue. If the impedance is low (within a range that may indicate contact with the tissue), the system may indicate contact. However, because the contact may be incomplete or less than sufficient, in some variations temperature may be used as a backup to confirm that the electrode is in contact with the tissue. For example, when the impedance of an electrode is low, the temperature at the electrode (e.g., at a corner of the electrode) may be compared to a threshold temperature to confirm contact. This threshold temperature is typically a constant (e.g., 16 degrees Celsius). For example, if the actual temperature is about or greater than about 16 degrees Celsius, then when the impedance is low, the system may indicate that the electrode is in sufficient contact.

This "constant temperature" threshold may introduce errors, however, particularly since the ambient temperature of the electrode may be greater than 16 degrees; even after operation of the electrode, when the electrodes are cooled by the application of coolant, the tip will warm up above this constant threshold.

As an alternative, the system may be configured so that the impedance measurement is unnecessary by utilizing just the temperature measurement and the time since last treatment (coolant) was applied.

For example, the system may track (e.g., using a timing element) the time since the last treatment, and apply a threshold based on the temperature of the tip (e.g., electrode) and the time since the last treatment. If a treatment has not taken place for ~30 seconds, the tip is likely to be approaching ambient temperature and should therefore use a steadily increasing temperature threshold. After ~3 minutes, the tip will be near the ambient temperature and the system may apply a fixed higher threshold that is above ambient (but below body temperature). If the elapsed time from the last treatment is less than a minimum time (~30 seconds), the tip temperature may still be below ambient and the temperature threshold can be set at a low value to minimize wait time for the next treatment cycle.

Figure 21:
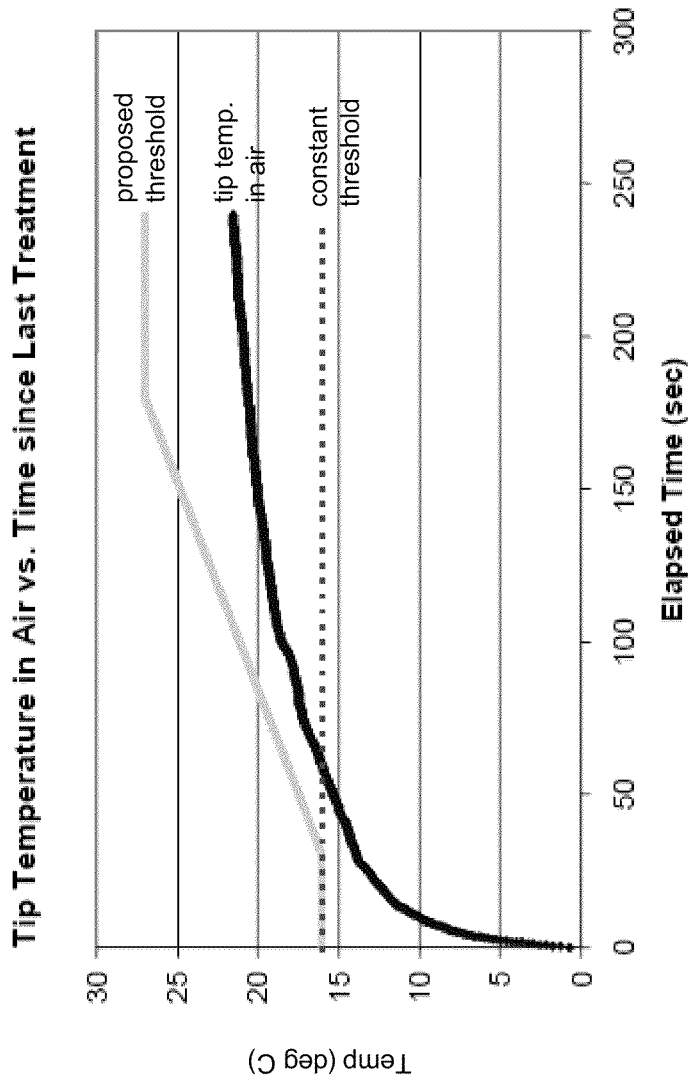
FIG. 21 is a graph showing the relationship of the temperature of the tip in air versus the time since last treatment, which may be used to calculate if an electrode is in sufficient contact with a tissue to initiate treatment.

For example, in one variation the system does not use impedance measurements to confirm contact, but relies only on temperature and time since last activation of the device (applying coolant). The temperature of an electrode may be compared to a temperature threshold that depends on the time since last activation of the device; this relationship may be a non-constant one. In particular, the relationship may describe temporal "regions" having different temperatures. In some variations the threshold relationship that is a step function, an arctan function, or other relationship. The threshold relationship may be referred to as a threshold function (which is a function of time) providing a threshold temperature. The threshold function is typically not a constant (over all time), although it may have temporal regions in which it is a constant. An exemplary threshold function is illustrated in FIG. 21 ("proposed threshold") and compared to the temperature of a tip in air and a constant threshold.

Table 1 illustrates the application of a threshold function to determine the tip is in sufficient contact with the tissue.

| Time since last Treatment | Temperature of electrode | Tissue Contact Determination |
|---|---|---|
| <30 seconds (value may be adjusted) | Each corner temperature of electrode is monitored: if T(corner) ≥16° C. (61° F.), then contact is okay otherwise contact is not okay | If 3 out of 4 corners are okay, then the tip is making acceptable contact otherwise the tip is not making acceptable contact |
| ≥30 seconds (value may be adjusted) | Each corner temperature is monitored: if T(corner) ≥ $T_{min}$, then contact is okay else contact is not okay. In one example, $T_{min}$ is a ramping threshold that starts at 16° C. and goes up to 27° C. (81° F.) as time from the last treatment goes from 30 to 180 seconds | If 3 out of 4 corners are okay, then the tip is making acceptable contact otherwise the tip is not making acceptable contact |

The example in Table 1 assumes that if a treatment has not taken place for ~30 seconds, then the tip is approaching ambient temperature and therefore a steadily increasing temperature threshold should be applied to determine if the electrode is making sufficient contact with the patient (whose tissue will be at body temperature). After ~3 minutes, the tip will be near the ambient temperature and the system will use a fixed higher threshold that is above ambient (but below body temperature). If the elapsed time from the last treatment is less than a minimum time (~30 seconds), the tip temperature is still below ambient and the temperature threshold will remain at the low value to minimize wait time for the next treatment cycle.

In table one, the column titled "tissue contact determination" gives an example of the synthesis of multiple measurements of electrode/tip contact that may be used to determine if the overall tip contact is sufficient to proceed with the application of energy in the procedure. In this example, if over half (e.g., 3 out of 4) of the contact determinations (from four thermisters near the corners of each of the four electrodes) are above the threshold temperature from the threshold function, then the controller may allow (or simply advise in some variations) proceeding with treatment in the current position; otherwise treatment may not be permitted or advised. In some variations the number of "okay" contacts based on the application of the threshold function to a plurality of thermisters may be greater than some other percentage (e.g., 60%, 75%, 80%, 90%, etc.) or all of the thermisters must be above the threshold function temperature. In some variations the location of the thermistor may be weighted to determine whether to permit or advise the user to proceed with treatment. For example, thermisters forming a continuous horizontal (or continuous vertical) line across the tissue (representing immediately adjacent electrodes) may be weighted more heavily in determining sufficient contact to proceed with treatment.

FIG. 21 illustrates one variation of a proposed based on a threshold function (similar to the one outlined in Table 1, above) in comparison with the temperature of a tip and a constant threshold. Even without an impedance measurement that detects a tip in air, the steadily increasing temperature threshold shown by the threshold function of the proposed threshold in FIG. 21 may prevent a tip fully or partially in air from indicating a ready to treat status; ramping the threshold between 30 and 180 seconds since the last RF delivery may track the continual rise of a tip temperature in air. The proposed threshold curve (threshold function) can be tuned to optimize rejection of false contact sensing while minimizing the wait time for true contact sensing.

Other variations of system, treatment tip design, and associated methods of use can be employed to achieve the objectives of the invention without departing from the scope of the invention, as will be appreciated by those skilled in the art. The shape and dimensions of the apparatus, including the handle and tip, can also be adjusted to enhance the effectiveness of the treatment taking into consideration physiological and anatomical information. While various embodiments of the present invention have been shown and described herein, such embodiments are provided by way of example only. Any theories of operation or benefit offered therein are intended only as an aid in describing the invention; such theories and interpretation do not bind or limit the claims with regard to tissue remodeling brought about by the practice of the invention. Numerous variations, changes, and substitutions may occur to those skilled in the art without departing from the invention. It should be understood that various alternatives to the embodiments of the invention described herein may be employed in practicing the invention. It is intended that the scope of the invention, methods and structures within the scope of the invention includes equivalents.

What is claimed is:

1. An apparatus for remodeling a therapeutic zone within tissue underlying a mucosal epithelium of female genital tissue, the apparatus comprising:
   an elongate handle configured to be held;
   a treatment tip, the tip comprising:
      a shaft comprising a longitudinal axis;
      an energy delivery element having an epithelium-contacting surface, the epithelium-contacting surface having a plurality of energy applicator regions; and
      an internal cooling chamber configured to internally cool the energy delivery element,
      wherein the energy delivery element comprises a thermally-conductive surface that is adapted to allow cooling of the epithelium while transmitting RF energy to heat the target tissue;
   a controller configured to determine contact with a target tissue and generate a contact map comprising a graphical map representing relative positions of the plurality of energy applicator regions on the energy delivery element, the graphical map showing contact status of each of the energy applicator regions;
   wherein the controller is configured to determine a time since the energy delivery element of the treatment tip was last activated, take a temperature of one or more sites on the treatment tip, and determine if the energy delivery element is contact with the tissue without applying RF energy to the tissue by comparing the temperature of the one or more sites on the treatment tip to a threshold function for the time since the treatment tip was last activated, and indicate if the treatment energy delivery element is in contact with the tissue; and
   a display configured to display the contact map.

2. The apparatus of claim 1, wherein the energy delivery element is configured to be parallel to the longitudinal axis of the shaft.

3. The apparatus of claim 1, wherein the energy delivery element is configured to have a width of 0.75 cm to 1.25 cm.

4. The apparatus of claim 1, wherein the energy delivery element is configured to have a length of 1 cm to 3 cm.

5. The apparatus of claim 1, wherein the energy delivery element is configured to be flat.

6. The apparatus of claim 1, wherein the internal cooling chamber comprises a plurality of coolant nozzles configured to spray cooling fluid on an internal portion of the energy delivery element further wherein the nozzles project at different angles relative to the energy delivery element.

7. The apparatus of claim 6, wherein the plurality of coolant nozzles comprises three coolant nozzles.

8. The apparatus of claim 1, wherein the energy delivery element comprises at least one RF electrode.

9. The apparatus of claim 1, further comprising at least one temperature sensor located in close proximity to the energy delivery element.

10. The apparatus of claim 1, further comprising a return coolant pathway extending proximally from the elongate handle configured to channel the used coolant away from a patient.

11. The apparatus of claim 1, further comprising a flat cable connecting the handle to the controller, the cable including a coolant delivery channel and a coolant return channel, at least one RF power line.

12. The apparatus of claim 1, wherein the handle does not include a button or switch controlling the application of RF energy.

13. A system for remodeling a therapeutic zone within tissue underlying a mucosal epithelium of female genital tissue, the system comprising:
- an elongate handle configured to be held, wherein the handle extends in a longitudinal direction;
- a treatment tip, wherein the tip comprising:
  - a plurality of energy-delivery elements having epithelium-contacting surfaces,
  - at least one internal cooling chamber configured to internally cool the energy delivery elements, wherein the energy delivery element comprises a thermally-conductive surface that is adapted to allow cooling of the epithelium while transmitting RF energy to heat the target tissue; and
- an integrated controller including:
  - a housing;
  - an RF generator within the housing;
  - a cooling sub-system within the housing;
  - a controller for controlling operation of the treatment tip and determining when the treatment tip is in contact with a target tissue and generating a contact map comprising a graphical map representing the position of the plurality of energy-delivery elements on the treatment tip having epithelium-contacting surfaces, the graphical map showing contact status of each of the energy applicator regions;
    - wherein the controller is configured to determine a time since at least one of the plurality of energy-delivery elements was last activated, take a temperature of one or more sites on the treatment tip, and determine if the at least one of the plurality of energy-delivery elements is in contact with the tissue without applying RF energy to the tissue by comparing the temperature of the one or more sites on the treatment tip to a threshold function for the time since the treatment tip was last activating, and indicate if the at least one of the plurality of energy-delivery elements is in contact with the tissue; and
  - a display configured to display the contact map.

14. The system of claim 13, further comprising a flat cable connecting the handle to the integrated controller, the cable including a coolant delivery channel and a coolant return channel, at least one RF power line.

15. The system of claim 13, further comprising a foot switch configured to connect to the integrated controller and trigger the application of RF energy by the plurality of energy-delivery elements.

16. The system of claim 13, wherein the display is configured to display control information.

17. The system of claim 13, wherein the integrated controller is portable.

18. The system of claim 13, wherein the system weighs less than fifty pounds.

* * * * *